(12) United States Patent
Tsang et al.

(10) Patent No.: US 9,212,379 B2
(45) Date of Patent: Dec. 15, 2015

(54) NUTRIENT MONITORING AND FEEDBACK CONTROL FOR INCREASED BIOPRODUCT PRODUCTION

(71) Applicant: Biogen Idec MA Inc., Cambridge, MA (US)

(72) Inventors: Valerie Liu Tsang, Carlsbad, CA (US); Angela Xiaoying Wang, Cardiff by the Sea, CA (US); Helena Yusuf-Makagiansar, San Diego, CA (US)

(73) Assignee: Biogen Idec MA Inc., Cambridge, MA (US)

( * ) Notice: Subject to any disclaimer, the term of this patent is extended or adjusted under 35 U.S.C. 154(b) by 478 days.

(21) Appl. No.: 13/659,655

(22) Filed: Oct. 24, 2012

(65) Prior Publication Data
US 2013/0065219 A1 Mar. 14, 2013

Related U.S. Application Data

(62) Division of application No. 12/538,036, filed on Aug. 7, 2009, now Pat. No. 8,318,416.

(60) Provisional application No. 61/087,598, filed on Aug. 8, 2008.

(51) Int. Cl.
*C12P 21/02* (2006.01)
*C07K 16/00* (2006.01)

(52) U.S. Cl.
CPC .................. *C12P 21/02* (2013.01); *C07K 16/00* (2013.01); *Y10T 436/115831* (2015.01); *Y10T 436/116664* (2015.01); *Y10T 436/117497* (2015.01); *Y10T 436/12* (2015.01)

(58) Field of Classification Search
None
See application file for complete search history.

(56) References Cited

U.S. PATENT DOCUMENTS

| | | | |
|---|---|---|---|
| 4,780,191 | A | 10/1988 | Romette et al. |
| 5,856,179 | A | 1/1999 | Chen et al. |
| 6,156,570 | A | 12/2000 | Hu et al. |
| 7,300,773 | B2 | 11/2007 | Drapeau et al. |
| 8,318,416 | B2 | 11/2012 | Tsang et al. |
| 2005/0070013 | A1 | 3/2005 | Luan et al. |
| 2010/0184624 | A1 | 7/2010 | Samuel et al. |

FOREIGN PATENT DOCUMENTS

| | | |
|---|---|---|
| WO | WO 02/101019 A2 | 12/2002 |
| WO | WO 2004/058800 A1 | 7/2004 |
| WO | WO 2006/026447 A2 | 3/2006 |

OTHER PUBLICATIONS

Kim, B.S., et al, "Production of poly(3-hydroxybutyric acid) by fed-batch culture of *Alcaligenes eutrophus* with glucose concentration control," *Biotechnol. Bioeng.* 43(9):892-8, John Wiley & Sons, Inc., United States (Apr. 1994).

Park, Y.S., et al., "Enhanced β-galactosidase production by high cell-density culture of recombinant *Bacillus subtilis* with glucose concentration control," *Biotechnol. Bioeng.* 40(6):686-96, John Wiley & Sons, Inc., United States (Sep. 1992).

International Search Report for International Patent Application No. PCT/US2009/004558, European Patent Office, Rijswijk, Netherlands, mailed on Mar. 30, 2010.

Written Opinion of the International Searching Authority for International Patent Application No. PCT/US2009/004558, European Patent Office, Munich, Germany, issued Feb. 8, 2011.

*Primary Examiner* — Jim Ketter
(74) *Attorney, Agent, or Firm* — Sterne, Kessler, Goldstein & Fox P.L.L.C.

(57) ABSTRACT

The present invention pertains to methods of increasing the efficiency of producing a bioproduct. In some embodiments, the method increases the quantity of a bioproduct produced, or decreases bioproduct production time, in a bioreactor cell culture producing the bioproduct, the method comprising, (a) intermittently or continuously analyzing the concentration of one or more nutrients in the bioreactor cell culture; and (b) adding to the bioreactor cell culture additional nutrient media when the concentration of the one or more nutrients is lower than a target value.

16 Claims, 13 Drawing Sheets

FIG. 7C
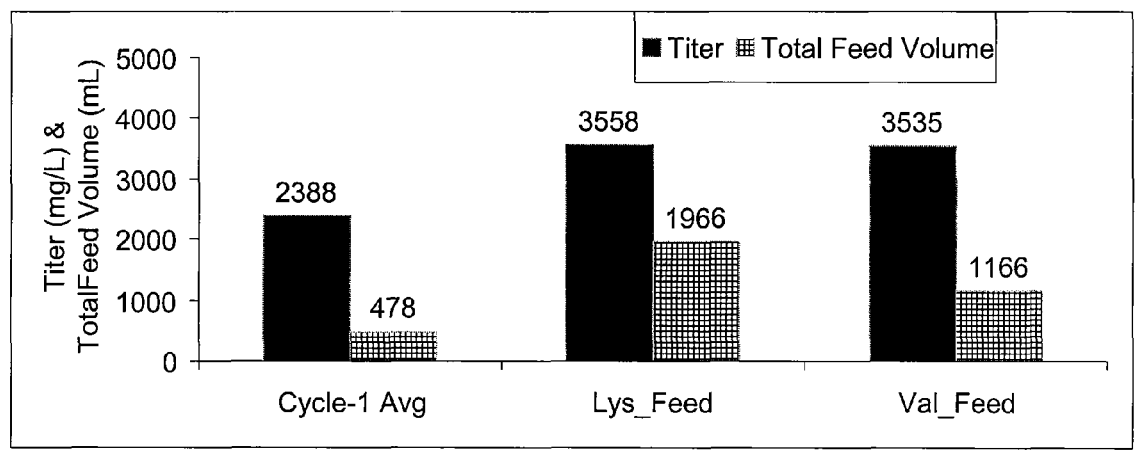
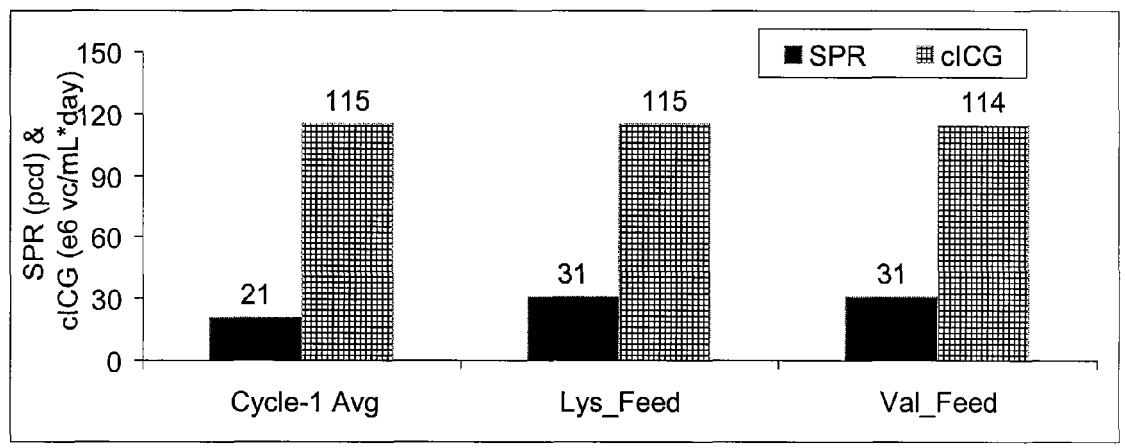

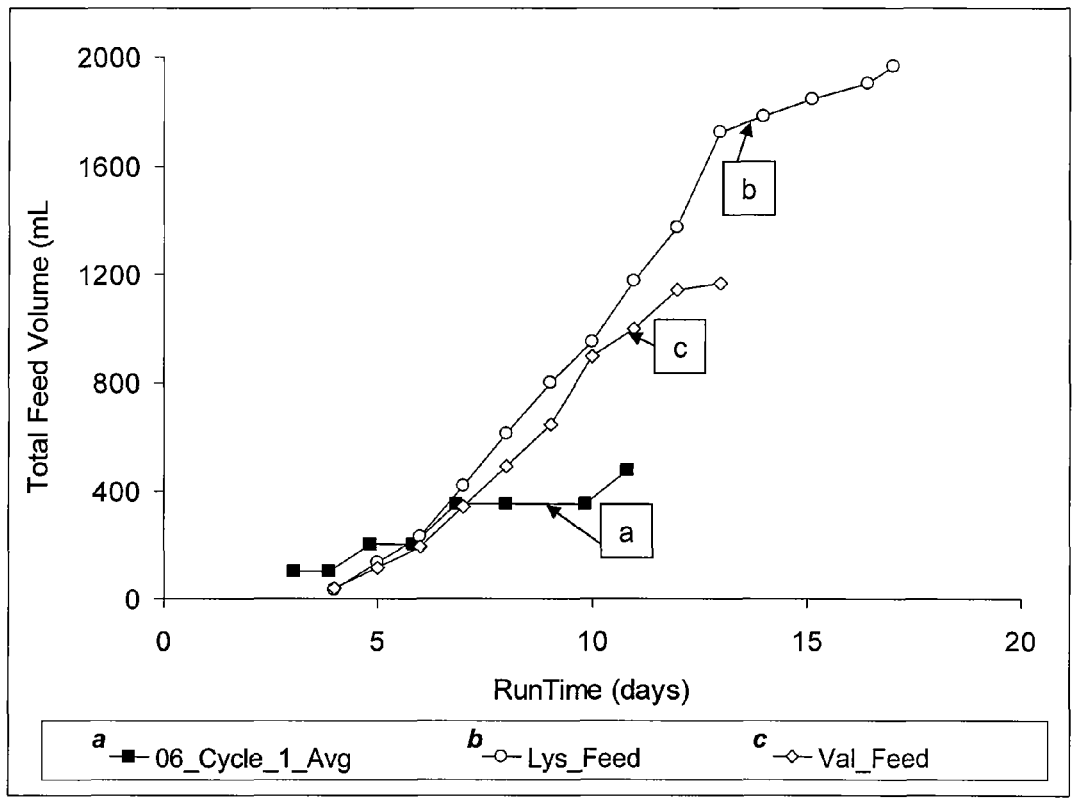
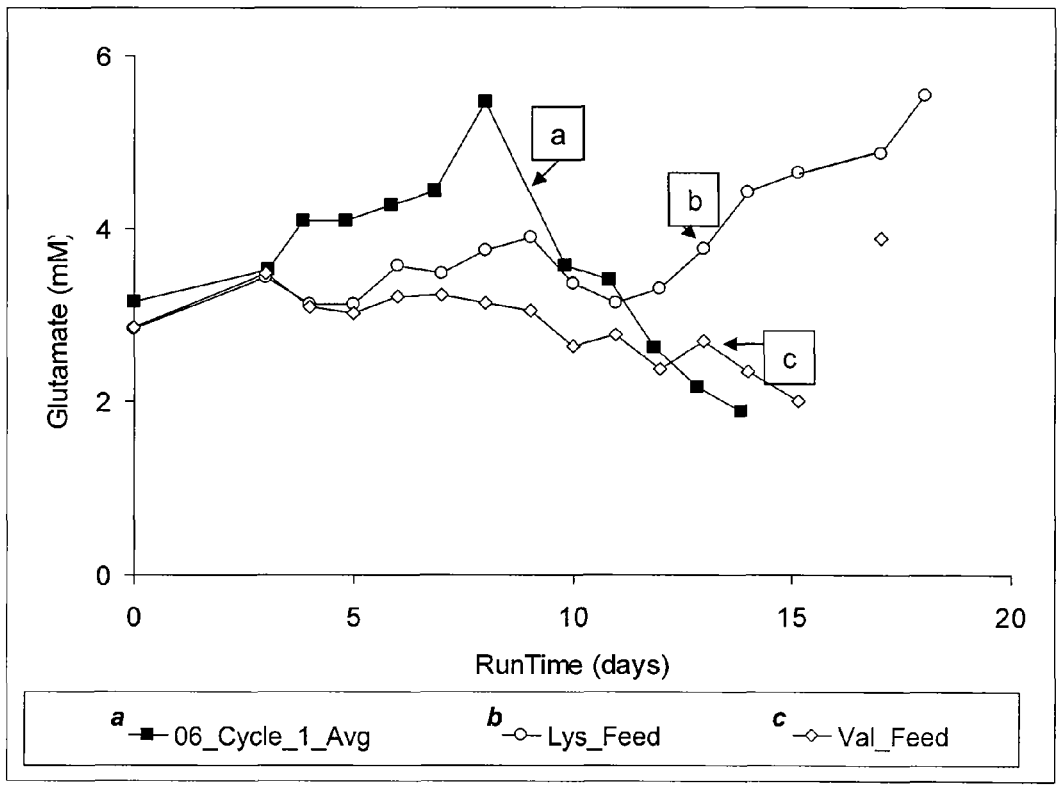

FIG. 9F
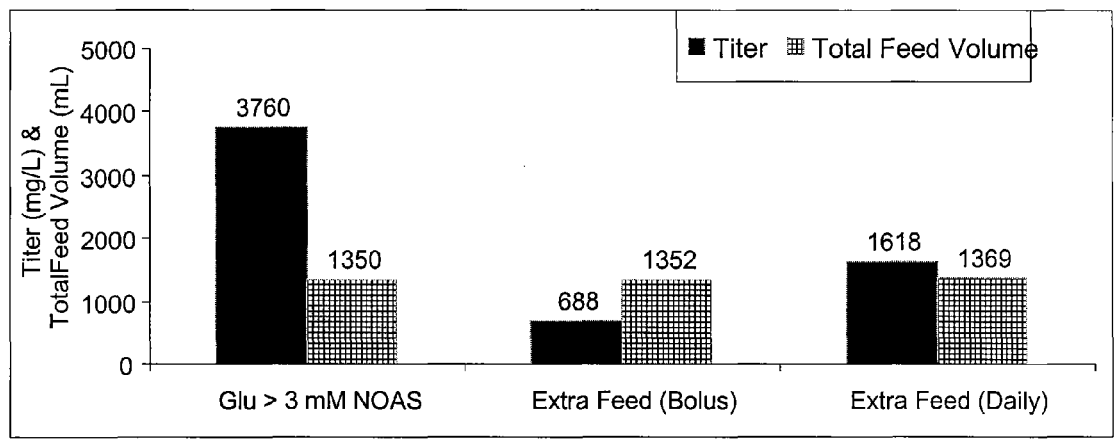
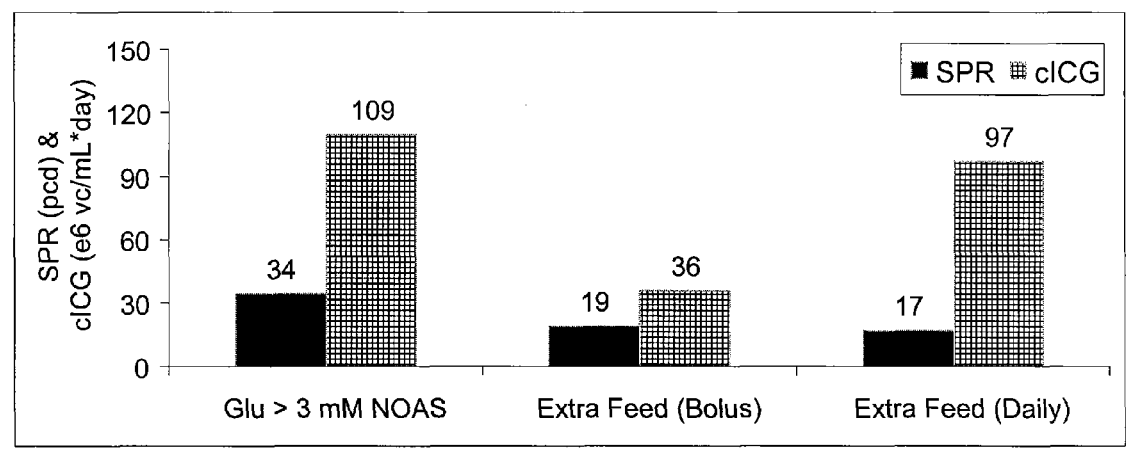

NUTRIENT MONITORING AND FEEDBACK CONTROL FOR INCREASED BIOPRODUCT PRODUCTION

CROSS REFERENCE TO RELATED APPLICATIONS

The present application is a divisional of U.S. application Ser. No. 12/538,036, filed Aug. 7, 2009, which claims the benefit of the filing date of U.S. Provisional Application No. 61/087,598, filed Aug. 8, 2008, each of which is incorporated herein by reference in its entirety.

BACKGROUND OF THE INVENTION

1. Field of the Invention

The present invention relates to methods of increasing the efficiency of producing a bioproduct. In some embodiments, the method increases the quantity of a bioproduct produced, or decreases bioproduct production time, in a bioreactor cell culture producing the bioproduct, the method comprising, (a) intermittently or continuously analyzing the concentration of one or more nutrient in the bioreactor cell culture; and (b) adding to the bioreactor cell culture additional nutrient media when the concentration of the one or more nutrients is lower than a target value.

2. Background Art

Conventional bioproduct manufacturing using bioreactors often utilizes various analytical tools to optimize growth conditions and monitor cell vitality. These analytical tools have included online sensors to detect pH or oxygen and offline assays to determine growth conditions (e.g., cell density or viability) or metabolite concentrations. In some instances, samples are collected during the bioreactor run, and then analyzed after the bioreactor run has finished. Data from these post-experimental assays are often used in future bioreactor runs.

The analytical tools used in conventional bioproduct manufacturing can be time consuming and can require a large amount of manual labor. Additionally, often the data obtained from the analytical tools is retrospective, and cannot be used to increase the efficiency of the bioreactor run from which they were obtained. Other analytical tools can be used in real time, but may not provide guidance for the most efficient method of bioproduct production. For example, traditional manufacturing processes have monitored oxygen levels (or $CO_2$ levels) and/or metabolite levels (e.g., lactic acid) during a bioreactor runs.

Although conventional approaches have been successful in providing quality bioproducts to the public, significant opportunities still exist for improving bioproducts development, manufacturing, and quality assurance through innovation in product and process development, process analysis, and process control.

BRIEF SUMMARY OF THE INVENTION

The present invention is related to a method of increasing the efficiency of producing a bioproduct. In some embodiments, the invention is related to a method of increasing the quantity of a bioproduct produced, or decreasing bioproduct production time, in a bioreactor cell culture producing the bioproduct, the method comprising: (a) intermittently or continuously analyzing the concentration of one or more nutrients in the bioreactor cell culture; and (b) adding to the bioreactor cell culture additional nutrient media when the concentration of the one or more nutrients is lower than a target value.

The method of the present invention can also comprise: (a) extracting a sample from the bioreactor cell culture by means of an online sample collection device; (b) analyzing the extracted sample by means of an analytical device to generate data representative of the quantity of a nutrient; (c) processing the generated data by means of an algorithm or computer-based processing program wherein the processed data is used to determine an amount of additional nutrient media to add to the bioreactor; and (d) adding the amount of additional nutrient media determined in (c) to the bioreactor by means of a feed device.

In some embodiments, the nutrient media is added to the bioreactor cell culture based on analysis of the concentration of only one amino acid, other nutrient or other surrogate marker. In some embodiments, the nutrient is a nutrient that is consumed during the bioreactor cell culture and that is a component of the nutrient media. In some embodiments, additional nutrient media is added to the bioreactor cell culture in an amount sufficient to maintain a substantially stable concentration of the amino acid throughout a bioreactor process. In some aspects of the invention, the nutrient is a carbohydrate source, an amino acid, a vitamin, or a combination thereof. In some particular aspects of the invention, the amino acid analyzed is glutamate, glutamine, lysine, leucine, tyrosine, valine, or combinations thereof, or alternatively, glutamate or glutamine. In other particular aspects of the invention, the carbohydrate source is glucose, galactose, maltose, or fructose.

Various cell cultures can be used in the bioreactor of the present invention. In some embodiments, the bioreactor cell culture comprises Chinese Hamster Ovary (CHO) cells, HEK-293 cells, or VERO cells. In some embodiments, the bioproduct is an antibody or antibody-like polypeptide.

The steps of the method of the present inventions can be repeated, and can occur at various intervals. In some embodiments, steps (a) and (b) or steps (a) to (d) are repeated greater than 10 times throughout a bioreactor process. In some embodiments, steps (a) and (b) or steps (a) to (d) are repeated every 4 minutes to every 18 hours throughout a bioreactor process, or every 10 minutes to 6 hour throughout a bioreactor process. The steps of the method of the present inventions can occur in a relatively short amount of time. In some embodiments, steps (a) and (b) or steps (a) to (d) are performed within about 1 minute to about 1 hour. In some embodiments, one or more steps in (a), (b), (c) or (d) are performed by one or more automated devices.

The methods of the present invention can be performed in the presence of any cell culture media. For example, in some embodiments of the invention, the bioreactor process is performed in the presence of serum-free media, protein-free media (including, but not limited, to protein-free media containing protein hydrolysates), or chemically defined media.

Various analytical devices can be used in the present invention. Such devices can include any instrument or process that can detect and/or quantify a surrogate molecule or marker, e.g., an amino acid or other substituents of cell culture media (e.g., a vitamin, a mineral, an ion, sugar, etc.). In some embodiments, the analytical device is an apparatus for performing gas chromatography, HPLC, cation exchange chromatography, anion exchange chromatography, size exclusion chromatography, an enzyme-catalyzed assay, and/or a chemical reaction assay.

In some embodiments, the present invention is directed to a method of efficiently producing an antibody. For example, the method can comprise: (a) sterilely extracting a sample from the bioreactor cell culture by means of an automated online sample collection device; (b) analyzing the extracted sample by means of an automated analytical device to generate data representative of the quantity of an amino acid; (c) processing the generated data by means of an algorithm or computer-based processing program wherein the processed data is used to determine an amount of additional nutrient media to add to the bioreactor; and (d) adding the amount of additional nutrient media determined in (c) to the bioreactor by means of an automated feed device.

The present invention can also be directed to a method of increasing production in subsequent bioreactor cell cultures. For example, the invention can be directed to a method of enhancing the quantity of an antibody (or other bioproduct) produced, or decreasing antibody (or other bioproduct) production time, in a bioreactor cell culture producing the antibody (or other bioproduct), the method comprising: (a) producing a first bioreactor cell culture by: (i) analyzing a sample (with or without extracting a sample from the bioreactor) by means of an automated sampling device (such as, for example, by means of off-line, on-line, in-line or at-line sample analysis); (ii) analyzing the sample by means of an automated analytical device to generate data representative of the quantity of a nutrient (or other surrogate marker); (iii) processing the generated data by means of an algorithm or computer-based processing program wherein the processed data is used to determine an amount of additional nutrient media to add to the bioreactor; (iv) adding the amount of nutrient media determined in (iii) to the bioreactor by means of an automated feed device; and (v) recording the time and amount of each nutrient media addition; and (b) performing one or more subsequent bioreactor cell culture processes, wherein the time and amount of each nutrient media addition in the subsequent bioreactor cell culture process is determined based on the time and amount of each nutrient media addition in the first bioreactor cell culture process. In some embodiments, the bioreactor of the first cell culture process is smaller than the bioreactor of the subsequent cell culture.

The present invention is also directed to methods of identifying a nutrient (or other surrogate marker) that is useful as a monitor for feedback control in a bioreactor cell culture method. The method can comprise: (a) intermittently or continuously analyzing the concentration of a nutrient (or other surrogate marker) during a bioreactor cell culture process; (b) adding nutrient media during the bioreactor cell culture process such that the nutrient (or other surrogate marker) levels are maintained above a target level; (c) determining the amount of a bioproduct produced over a period of time during the bioreactor cell culture process; and (d) comparing the amount of bioproduct produced over the same period of time in a control bioproduct cell culture process, wherein an increase in the amount of bioproduct produced or a decrease in the bioproduct production time compared to the control indicates that the nutrient (or other surrogate marker) can be used as a signal for feedback control in a bioreactor cell culture process.

The invention can also be directed to a bioproduct produced by the methods of the present invention.

BRIEF DESCRIPTION OF THE DRAWINGS/FIGURES

Figure 5A:
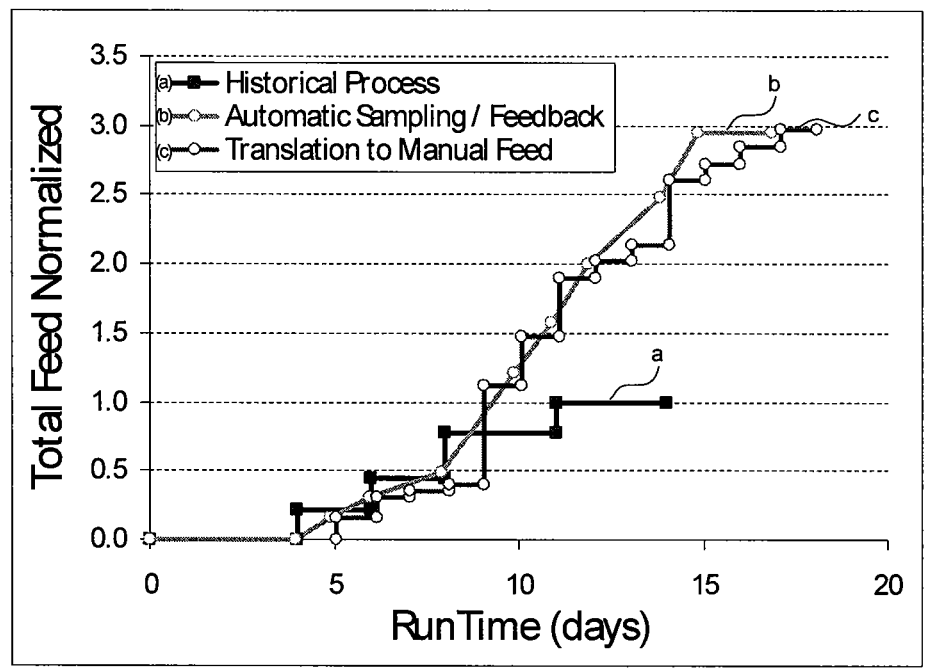
Figure 5B:
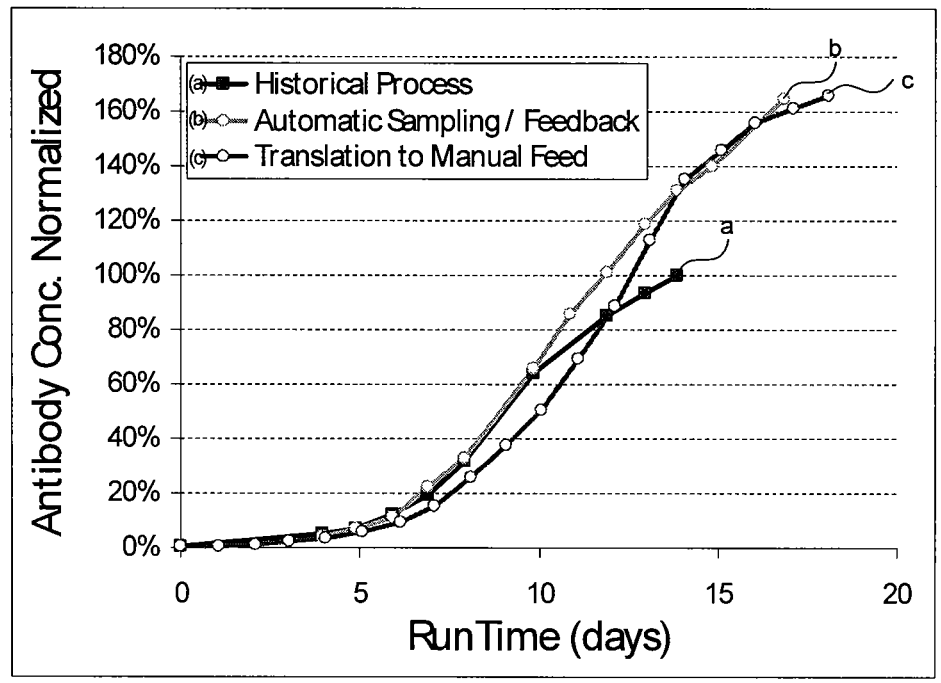

FIG. 5A compares (a) the total feed added in a traditional manufacturing process, (b) the total feed added in a automatic sampling/feedback control process of the present invention, and (c) a manual feed process utilizing the feeding strategy developed from an automatic sampling/feedback control process. FIG. 5B compares (a) the antibody concentration in the bioreactor produced in a traditional manufacturing process, (b) the antibody concentration in the bioreactor produced in a automatic sampling/feedback control process of the present invention, and (c) a manual feed process utilizing the feeding strategy developed from an automatic sampling/feedback control process.

Figure 6A:
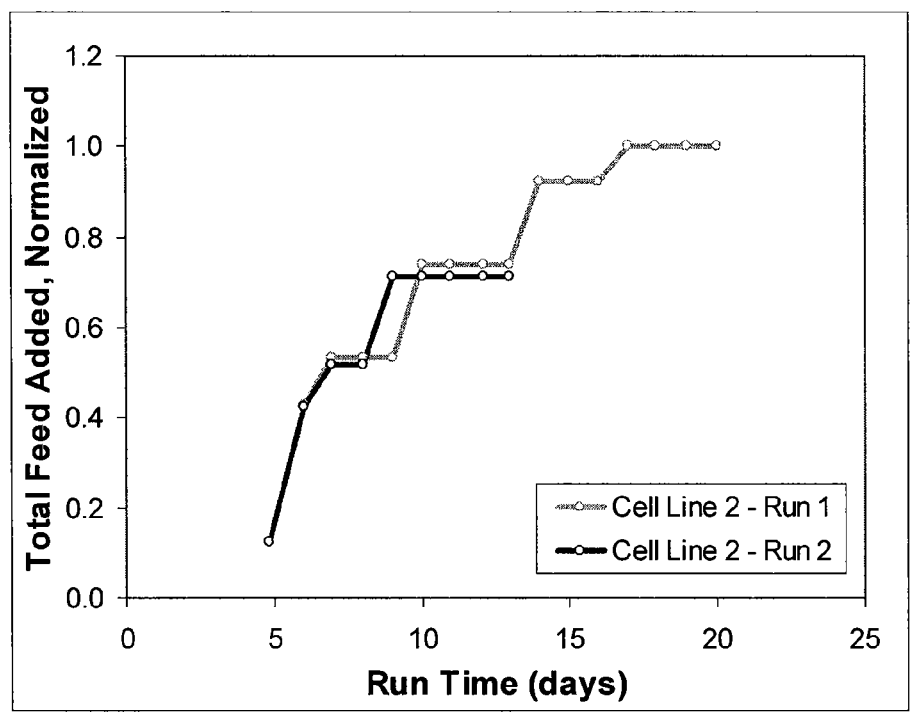
Figure 6B:
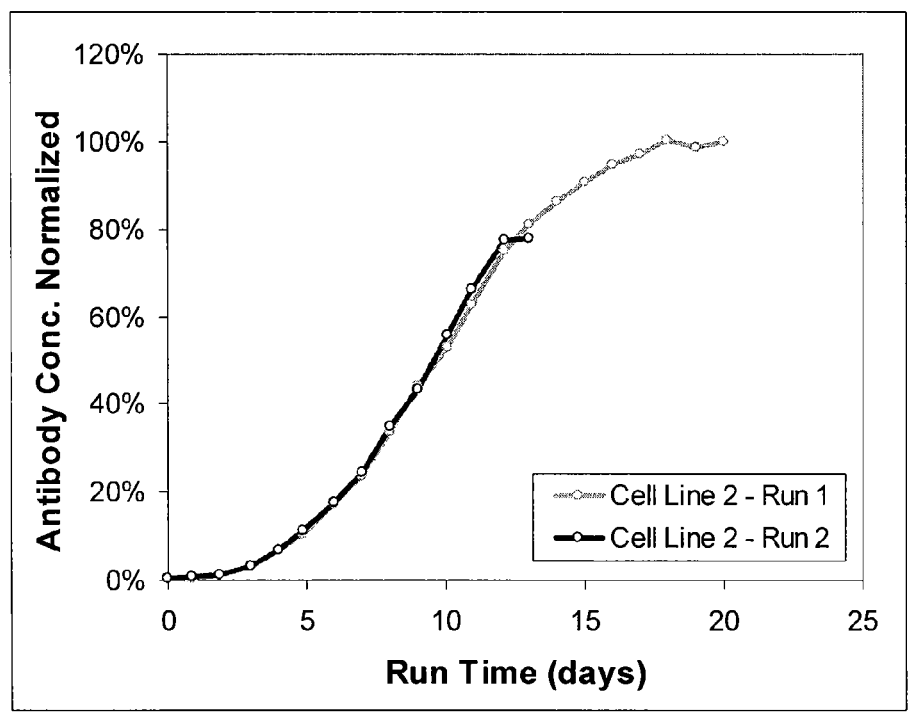

FIG. 6A depicts (a) the total feed added in a first cell line which uses the automatic sampling/feedback control process of the present invention, and (b) the total feed added to a second cell line which uses the automatic feedback strategy from the first cell line. FIG. 6B depicts (a) the antibody concentration in a bioreactor having a first cell line which uses the automatic sampling/feedback control process of the present invention, and (b) the antibody concentration in a bioreactor having a second cell line which uses the automatic feedback strategy from the first cell line.

Figure 7A:
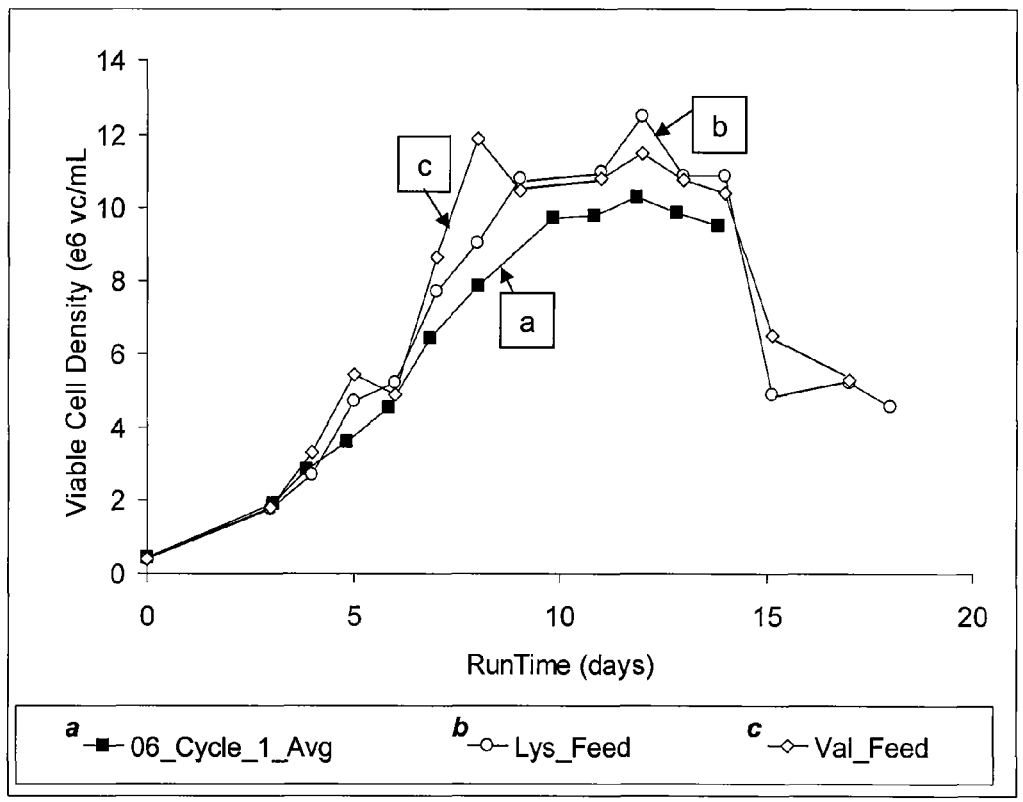
Figure 7B:
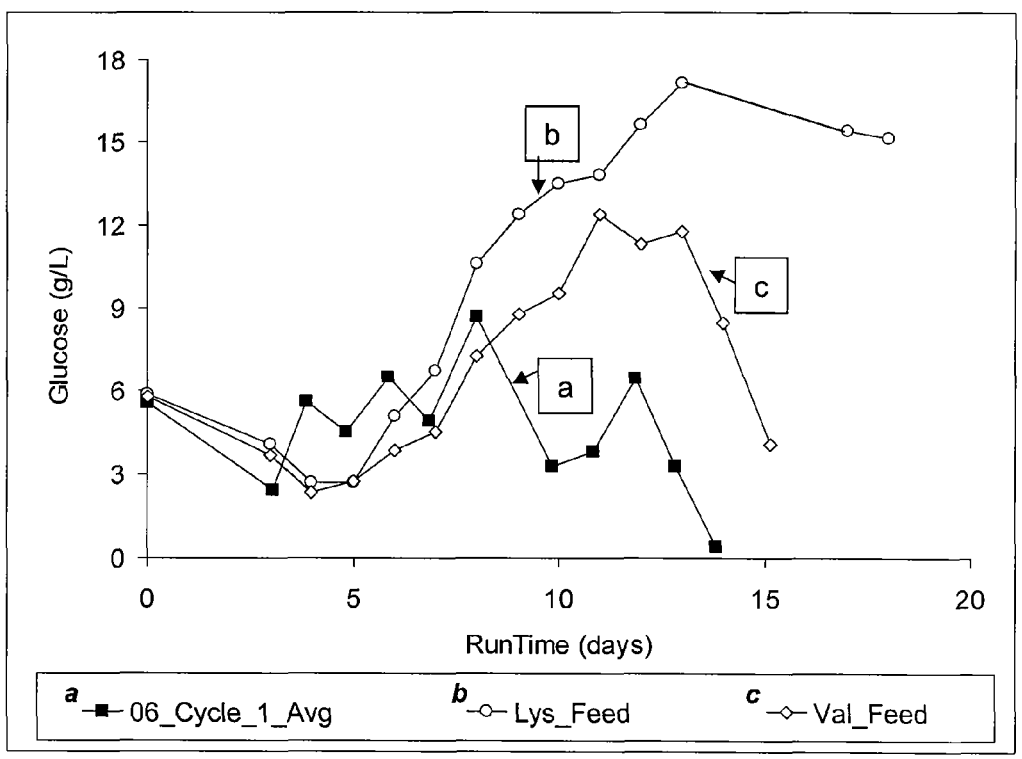

FIG. 7A depicts the viable cell density measured over time in cell cultures using (a) a traditional manufacturing process ("06_Cycle_1_Avg") (b) a lysine control process, and (c) a valine control process. FIG. 7B depicts the glucose concentration measured over time in cell cultures using (a) a traditional manufacturing process, (b) a lysine control process, and (c) a valine control process. FIG. 7C depicts the titer, total feed volume, specific productivity rate (SPR), and cumulative integrated cell growth (cICG) measured in each of the cell cultures.

FIG. 8A shows the total feed volume added to cell cultures using (a) a traditional manufacturing process, (b) a lysine control process, and (c) a valine control process. FIG. 8B shows the glutamate concentration measured over time in each of the cell cultures.

Figure 9A:
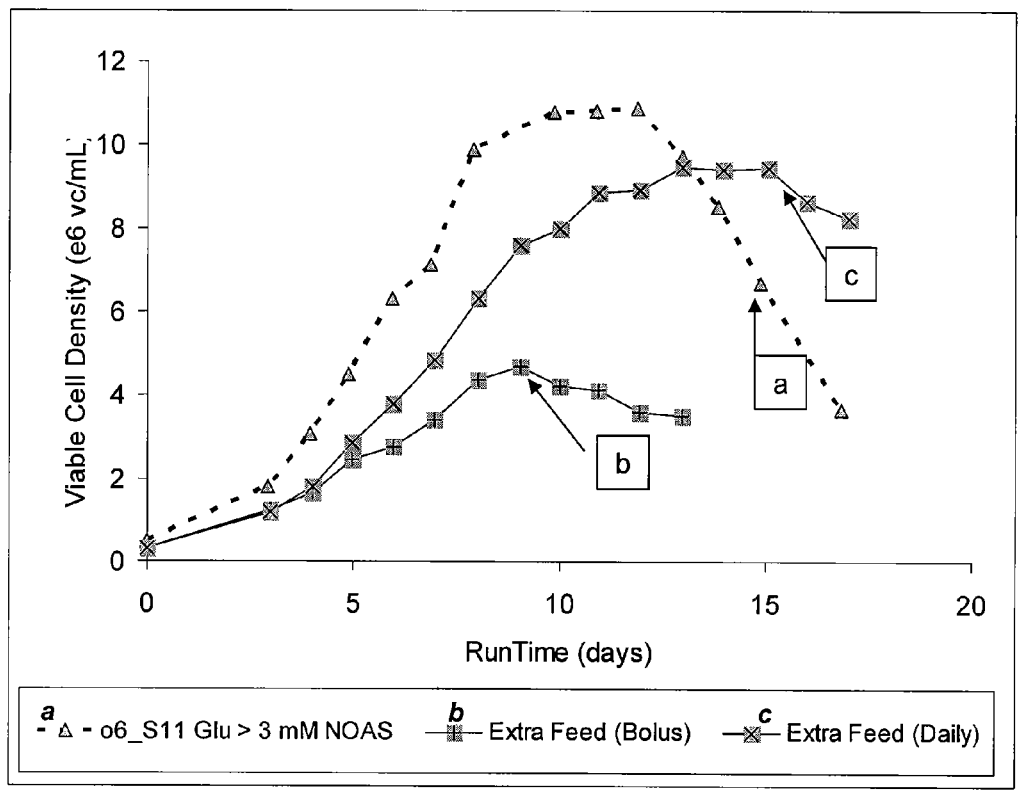
Figure 9B:
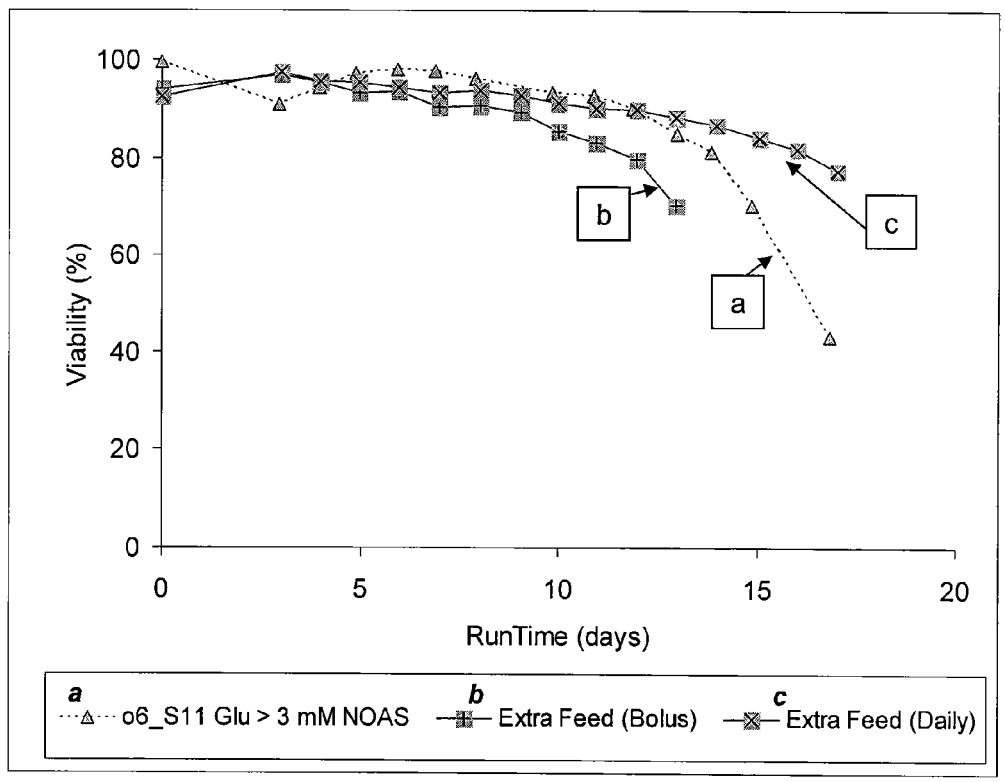
Figure 9C:
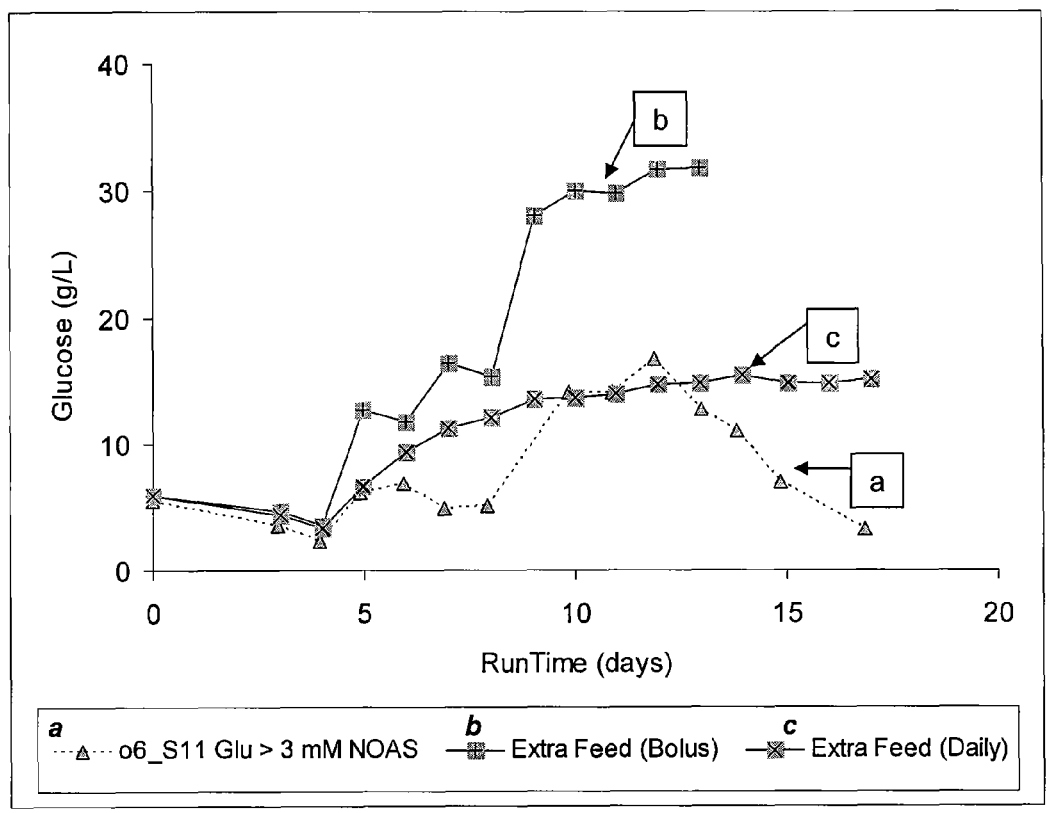
Figure 9D:
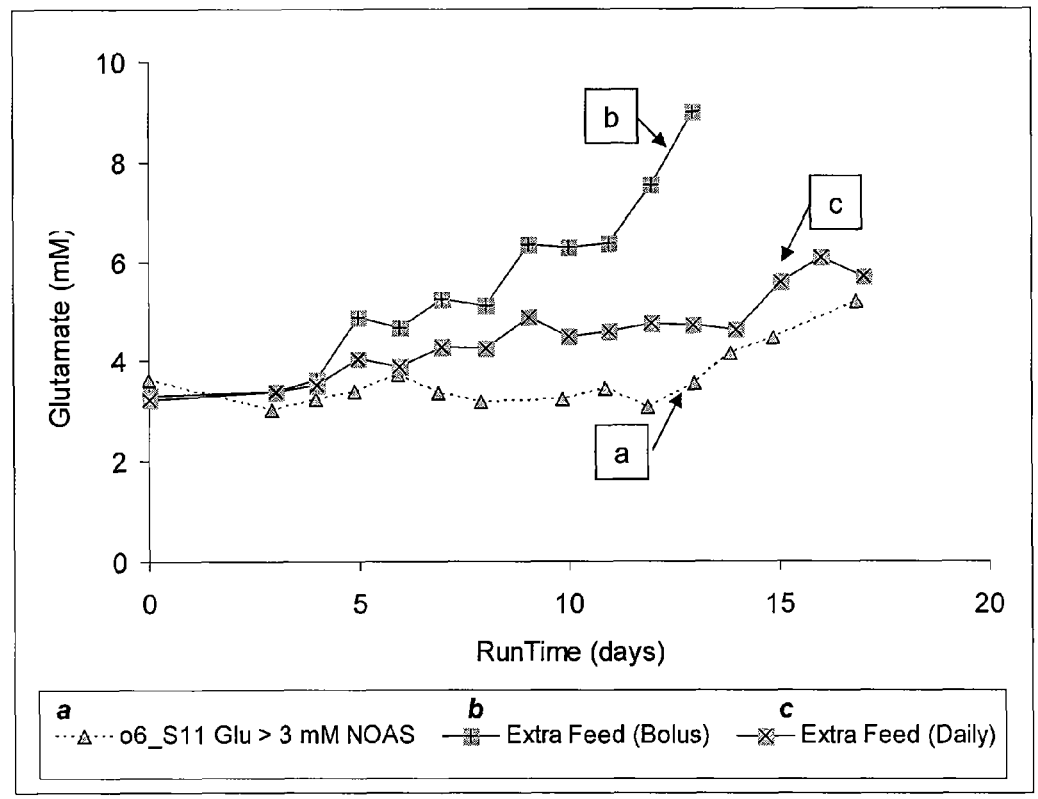
Figure 9E:
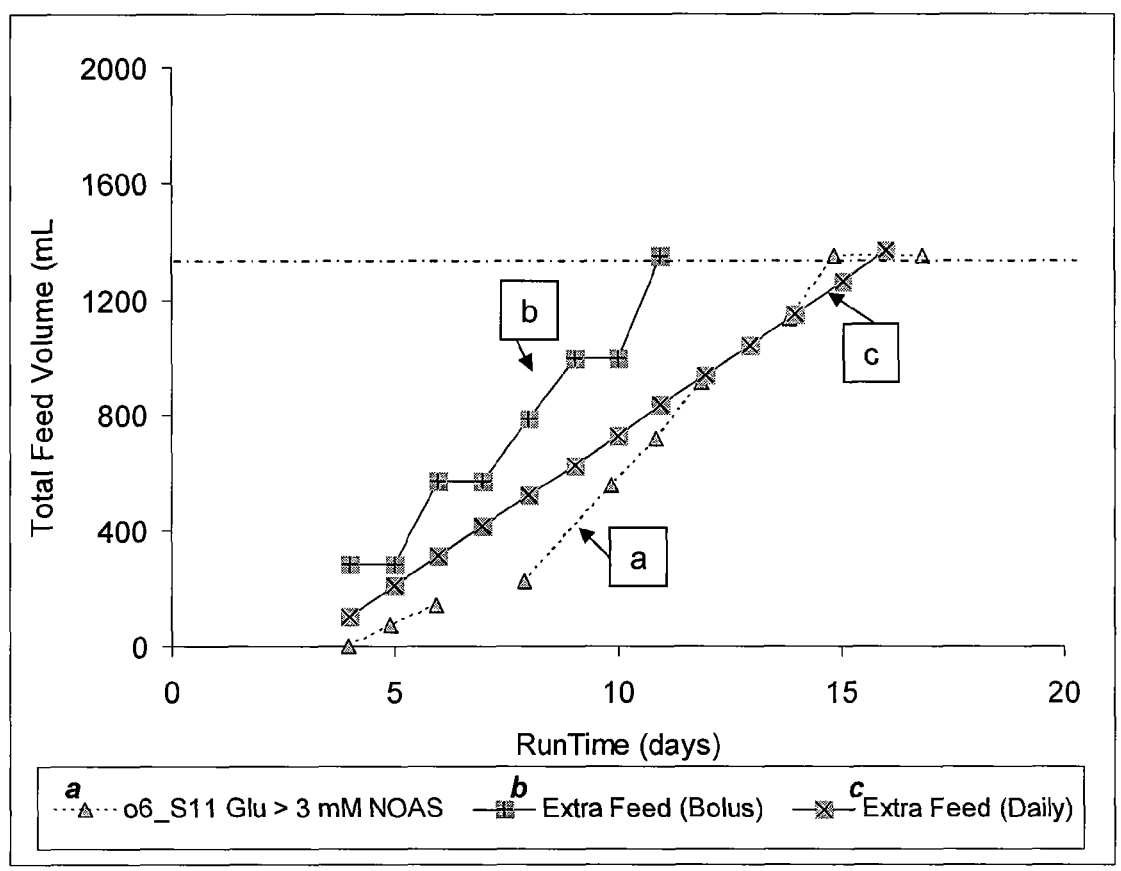

FIG. 9A shows the viable cell density measured over time in cell cultures using (a) an autosampling glutamate control process, (b) a bolus extra feed process, and (c) a daily extra feed process. FIG. 9B shows the percent cell viability over time in each of the cell cultures. FIG. 9C shows the glucose concentration over time in each of the cell cultures. FIG. 9D shows the glutamate concentration over time in each of the cell cultures. FIG. 9E shows the total feed volume over time in each of the cell cultures. FIG. 9F shows the titer, total feed volume, specific productivity rate (SPR), and cumulative integrated cell growth (cICG) measured in each of the cell cultures.

DETAILED DESCRIPTION OF THE INVENTION

The present invention is related to a method of increasing the efficiency of producing a bioproduct. In some embodiments, the invention is related to a method of increasing the quantity of a bioproduct produced, or decreasing bioproduct production time, in a bioreactor cell culture producing the bioproduct, the method comprising: (a) intermittently or continuously analyzing the concentration of one or more nutrient (or other surrogate markers) in the bioreactor cell culture; and (b) adding to the bioreactor cell culture additional nutrient media when the concentration of the one or more nutrients (or other surrogate markers) is lower than a target value.

The method of the present invention can be directed to a method comprising: (a) extracting a sample from the bioreactor cell culture by means of an online sample collection device; (b) analyzing the extracted sample by means of an analytical device to generate data representative of the quantity of a nutrient; (c) processing the generated data by means of an algorithm or computer-based processing program wherein the processed data is used to determine an amount of additional nutrient media to add to the bioreactor; and (d) adding the amount of additional nutrient media determined in (c) to the bioreactor by means of a feed device.

The method of the present invention can also comprise: (a) analyzing a sample in a bioreactor cell culture by extracting or not extracting a sample from the bioreactor cell culture by means of an off-line, on-line, in-line, or at-line analytical device; (b) analyzing the sample by means of an analytical device to generate data representative of the quantity of a nutrient (or other surrogate marker); (c) processing the generated data by means of an algorithm or computer-based processing program wherein the processed data is used to determine an amount of additional nutrient media to add to the bioreactor; and (d) adding the amount of additional nutrient media determined in (c) to the bioreactor by means of a feed device.

The present invention can also be directed to a method of increasing production in subsequent bioreactor cell cultures. For example, the invention can be directed to a method of enhancing the quantity of an antibody (or other bioproduct) produced, or decreasing antibody (or other bioproduct) production time, in a bioreactor cell culture producing the antibody (or other bioproduct), the method comprising: (a) producing a first bioreactor cell culture by: (i) analyzing a sample (with or without extracting a sample from the bioreactor) by means of an automated sampling device (such as, for example, by means of off-line, on-line, in-line or at-line sample analysis); (ii) analyzing the sample by means of an automated analytical device to generate data representative of the quantity of a nutrient (or other surrogate marker); (iii) processing the generated data by means of an algorithm or computer-based processing program wherein the processed data is used to determine an amount of additional nutrient media to add to the bioreactor; (iv) adding the amount of nutrient media determined in (iii) to the bioreactor by means of an automated feed device; and (v) recording the time and amount of each nutrient media addition; and (b) performing one or more subsequent bioreactor cell culture processes, wherein the time and amount of each nutrient media addition in the subsequent bioreactor cell culture process is determined based on the time and amount of each nutrient media addition in the first bioreactor cell culture process. In some embodiments, the bioreactor of the first cell culture process is smaller than the bioreactor of the subsequent cell culture.

It is to be noted, unless otherwise clear from the context, that the term "a" or "an" entity refers to one or more of that entity; for example, "an amino acid," is understood to represent one or more proteins. As such, the terms "a" (or "an"), "one or more," and "at least one" can be used interchangeably herein.

Reference is made herein to a "traditional manufacturing process." This term refers to either the traditional processes of (a) adding nutrient media in bolus feeds to the bioreactor at designated time points, or (b) adding glucose (or another single nutrient) to the bioreactor as the glucose (or other single nutrient) is consumed. The traditional manufacturing processes lead to lower bioproduct yields and/or less efficient bioproduct production. The present invention utilizes a feedback control method, wherein the concentration of one or more nutrients is monitored, and based on the concentration of that nutrient, an appropriate amount of total media is added to the bioreactor. The monitoring can be done automatically and frequently, resulting in greatly increased yields of bioproduct.

In some embodiments, the nutrient media is added to the bioreactor cell culture based on analysis of the concentration of a surrogate marker (e.g., an amino acid or other nutrient). The term "surrogate marker" refers to a one or more molecules or compounds used to determine when and/or how much total nutrient media to add to a bioreactor during cell cultivation. For example, if glutamate is the surrogate marker, the total amount of total nutrient media added to a bioreactor is based upon the concentration of glutamate in the bioreactor. In some embodiments, the nutrient media is added to the bioreactor cell culture based on analysis of the concentration of a single surrogate marker, e.g., a single amino acid. In some embodiments, the nutrient media is added to the bioreactor cell culture based on analysis of the concentration of one to five or five to ten surrogate markers, e.g., five to ten different amino acids, other nutrients, or other surrogate markers. In some embodiments, the nutrient mediate added to the bioreactor cell culture is based on the concentration of any multiple of surrogate markers (e.g., in the range 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 2 to 20, 2 to 25, 2 to 30, 2 to 40, 2 to 50, 2 to 60, 2 to 70, 2 to 80, 2 to 90 or 2 to 100 different amino acids, other nutrients, or other surrogate markers).

The term nutrient refers to any compound, molecule, or substance used by an organism to live, grow, or otherwise add biomass. Examples of nutrients include carbohydrate sources (e.g., simple sugars such as glucose, galactose, maltose or fructose, or more complex sugars), amino acids, vitamins (e.g., B group vitamins (e.g., B12), vitamin A vitamin E, riboflavin, thiamine and biotin). In the present invention, one or more nutrients can be utilized as a surrogate molecule to determine the amount of total nutrient media to add to a bioreactor. In some embodiments, the term nutrient refers to simple sugars, vitamins, and amino acids.

The term "amino acid" refers any of the twenty standard amino acids, i.e., glycine, alanine, valine, leucine, isoleucine, methionine, proline, phenylalanine, tryptophan, serine, threonine, asparagine, glutamine, tyrosine, cysteine, lysine, arginine, histidine, aspartic acid and glutamic acid, single stereoisomers thereof, and racemic mixtures thereof. The term "amino acid" can also refer to the known non-standard amino acids, e.g., 4-hydroxyproline, $\epsilon$-N,N,N-trimethyllysine, 3-methylhistidine, 5-hydroxylysine, O-phosphoserine, $\gamma$-carboxyglutamate, $\epsilon$-N-acetyllysine, $\omega$-N-methylarginine, N-acetylserine, N,N,N-trimethylalanine, N-formylmethionine, $\gamma$-aminobutyric acid, histamine, dopamine, thyroxine, citrulline, ornithine, $\beta$-cyanoalanine, homocysteine, azaserine, and S-adenosylmethionine. In some embodiments, the amino acid is glutamate, glutamine, lysine, tyrosine or valine. In some embodiments, the amino acid is glutamate or glutamine.

Various concentrations of a surrogate marker, e.g., an amino acid, can be maintained in a bioreactor cell culture. The desired, or target, concentration of a surrogate marker, e.g., an amino acid, in the bioreactor cell culture can vary from cell line to cell line and is often known to those in the art or can be determined experimentally. In some embodiments, the target concentration of a surrogate marker, e.g., an amino acid, in a bioreactor cell culture is the concentration of the amino acid found in a commercially available media, or the media being used to originally cultivate the cell line. In some embodiments, the target concentration of a surrogate marker, e.g., an amino acid, in a bioreactor cell culture is the concentration of the amino acid used to cultivate the cell line, or a concentration ±10%, 20%, 30%, 40% the concentration of the amino acid used to cultivate the cell line. In some embodiments, the "target value" of a surrogate marker is the minimum concentration of surrogate marker sufficient to maintain the growth and propagation of the cell line. In some embodiments, the target value of a surrogate marker is a concentration of at least about 0.25 mM, at least about 0.5 mM, at least about 1 mM, at least about 2 mM, at least about 3 mM, at least about 4 mM, at least about 5 mM, or at least about 10 mM. In some embodiments, the target value of a surrogate marker is between about 0.25 mM and about 5 mM, between about 0.5 mM and about 5 mM, between about 1 mM and about 5 mM, between about 2 mM and about 5 mM, or between about 3 mM and about 5 mM.

The terms "nutrient media," "feed media," "feed," "total feed," and "total nutrient media" can be used interchangeably, and include a "complete" media used to grow, propagate, and add biomass to a cell line. Nutrient media is distinguished from a substance or simple media which by itself is not sufficient to grow and propagate a cell line. Thus, for example, glucose or simple sugars by themselves are not nutrient media, since in the absence of other required nutrients, they would not be sufficient to grow and propagate a cell line. One of skill in the art can appreciate that cells may continue to grow, live and propagate in the presence of incomplete media, but become instable and/or greatly reduce their growth rate. Thus, in some embodiments, the term "nutrient media" includes a media sufficient to grow, propagate, and add biomass to a cell line without a loss in stability, growth rate, or a reduction of any other indicators of cellular health for a period of at least 2 days, 3 days, 4 days, 5 days, 1 week, 2 weeks, or 3 weeks. In some embodiments, the term "nutrient media" includes a media which may lack one or more essential nutrients, but which can continue to grow, propagate, and add biomass to a cell line without a loss in stability, growth rate, or a reduction of any other indicators of cellular health for a period of at least 2 days, 3 days, 4 days, 5 days, 1 week, 2 weeks, or 3 weeks.

In some embodiments, the nutrient media is a cell culture media. Optimal cell culture media compositions vary according to the type of cell culture being propagated. In some embodiments, the nutrient media is a commercially available media. In some embodiments, the nutrient media contains e.g., inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. Examples of nutrient medias include, but are not limited to, basal media (e.g., MEM, DMEM, GMEM), complex media (RPMI 1640, Iscoves DMEM, Leibovitz L-15, Leibovitz L-15, TC 100), serum free media (e.g., CHO, Ham F10 and derivatives, Ham F12, DMEM/F12). Common buffers found in nutrient media include PBS, Hanks BSS, Earles salts, DPBS, HBSS, and EBSS. Media for culturing mammalian cells are well known in the art and are available from, e.g., Sigma-Aldrich Corporation (St. Louis, Mo.), HyClone (Logan, Utah), Invitrogen Corporation (Carlsbad, Calif.), Cambrex Corporation (E. Rutherford, N.J.), JRH Biosciences (Lenexa, Kans.), Irvine Scientific (Santa Ana, Calif.), and others. Other components found in nutrient media can include ascorbate, citrate, cysteine/cystine, glutamine, folic acid, glutathione, linoleic acid, linolenic acid, lipoic acid, oleic acid, palmitic acid, pyridoxal/pyridoxine, riboflavin, selenium, thiamine, and transferrin. In some embodiments the nutrient media is serum-free media, a protein-free media, or a chemically defined media. One of skill in the art will recognize that there are modifications to nutrient media which would fall within the scope of this invention.

In some embodiments, nutrient media is added to the bioreactor cell culture in an amount sufficient to maintain a substantially stable concentration of a surrogate marker, e.g., an amino acid, throughout a bioreactor process. In some embodiments, nutrient media is added to the bioreactor cell culture in an amount sufficient to maintain a minimum concentration, or target amount, of a surrogate marker, e.g., an amino acid, throughout a bioreactor process. In some aspects of the invention, the amino acid analyzed is glutamate, glutamine, tyrosine, lysine, leucine, valine, or combinations thereof.

The bioproduct of the present invention can be produced from various mammalian cell cultures. Mammalian cells of the present invention, include any mammalian cells that are capable of growing in culture. Exemplary mammalian cells include, e.g., CHO cells (including CHO-K1, CHO DUKX-B11, CHO DG44), VERO, BHK, HeLa, CV1 (including Cos; Cos-7), MDCK, 293, 3T3, C127, myeloma cell lines (especially murine), PC12, HEK-293 cells (including HEK-293T and HEK-293E), PER C6, Sp2/0, NS0 and W138 cells. Mammalian cells derived from any of the foregoing cells may also be used. In some embodiments, the bioreactor cell culture comprises Chinese Hamster Ovary (CHO) cells, HEK-293 cells, or VERO cells.

The steps of a method of the present inventions can be repeated, and can occur at various intervals. In some embodiments, steps (a) and (b) or steps (a) to (d) are repeated greater than 10 times throughout a bioreactor process, or 10 to 1000 times, 20 to 500 times or 30 to 100 times throughout a bioreactor process. In some embodiments, steps (a) and (b) or steps (a) to (d) are repeated about every 4 minutes, 10 minutes, 30 minutes, 60 minutes, 2 hours, 3 hours, 6 hours, 8 hours, 12 hour, 16 hours, 18 hours, or 24 hours throughout a bioreactor process, or about every 4 to 18 hours, or about every 10 minutes to about every 6 hours throughout a bioreactor process.

The steps of a method of the present inventions can occur in a relatively short amount of time, i.e., the sampling, analysis, and addition of additional nutrient media can occur relatively quickly. In some embodiments, steps (a) and (b) or steps (a) to (d) are performed within about 1 minute to about 2 hours, about 1 minute to about 1 hour, about 4 minutes to about 45 minutes, or about 10 minutes to about 30 minutes.

In some embodiments, one or more steps in (a), (b), (c) or (d) are performed by one or more automated devices. For purposes of the present description, "automatic", "automatically", or "automated" means that a mechanical device or devices perform a task or tasks without any human intervention or action (aside from the human intervention or action necessary to initially prepare the device or devices for task performance; or as may be required to maintain automatic operation of the device or devices). A "mechanical device" which performs a task (or tasks) automatically may, optionally, include a computer and the necessary instructions (code) therein to process collected data which may be used therein for decision making purposes to control and direct performance of the device or devices (for example, such as in controlling the timing, duration, frequency, kind, and/or character of tasks to be performed).

For example, one or more of the sample collection device, analytical device, processing program, or feed device can be automated. Thus, e.g., in some embodiments, the methods of the present invention can utilize an automated sample collection device and/or an analytical device that can be off-line, at-line, on-line or in-line, in order to reduce variability, to optimize or enhance quantity and/or quality of a bioproduct during (i.e., in the midst of) any or all steps in a bioproduct manufacturing process.

For purposes of the present description, "off-line" analysis is intended to indicate that a sample is permanently removed from the production process and analyzed apart therefrom at a later point in time such that the data analysis does not convey real-time or near real-time information about in-process conditions. In some embodiments, one or more analytical devices used in the method of the invention is off-line.

For purposes of the present description, "at-line" is intended to indicate that a sample is permanently removed from the production process but is analyzed in a time-frame in close proximity to the time in which it was removed, thereby, providing real-time or near-real time information which may be used to automatically control or change in-process conditions. "At-line" analysis may be performed in an automated or semi-automated fashion. In some embodiments, one or more of the analytical devices used in the method of the present invention is at-line.

For purposes of the present description, "on-line" is intended to indicate that a sample is diverted from the production process, is analyzed in a time-frame in close proximity to the time in which it was removed, thereby, providing real-time or near-real time information which may be used to automatically control or change in-process conditions, and wherein the sample may be (but is not necessarily) returned to the production process. "On-line" analysis may be performed in an automated or semi-automated fashion. In some embodiments, one or more of the analytical devices used in the method of the present invention is on-line.

For purposes of the present description, "in-line" is intended to indicate that a sample is not removed from the production process but, instead, the process "sample" is monitored in real-time by an invasive or non-invasive means, thereby, providing real-time or near-real time information which may be used to automatically control or change in-process conditions. For example, an analytical device (or a sensor-portion connected thereto) may be introduced directly into a bioreactor or purification unit, or the device or sensor-portion may be separated from the bioreactor or purification unit by an appropriate barrier or membrane. "In-line" analysis may be performed in an automated or semi-automated fashion. In-line and on-line analyses are advantageous because they can usually be performed at significantly higher frequency intervals (including continuously or discontinuously) compared to off-line and at-line analytical methods. In some embodiments, one or more of the analytical devices used in the method of the present invention is in-line.

In an exemplary embodiment of the methods of the present invention, it is envisioned that direct (at-line, in-line, or on-line) analysis of one or more surrogate marker, e.g., amino acid, concentrations in real time from bioreactor samples are utilized to implement automatic, dynamic feedback controlled addition of additional nutrient media.

Various analytical devices can be used in the present invention. Such devices can include any instrument or process that can detect and/or quantify a surrogate molecule, e.g., an amino acid or other substituents of cell culture media (e.g., a vitamin, a mineral, an ion, sugar, etc.). In some embodiments, the analytical device is an apparatus for performing gas chromatography, HPLC, cation exchange chromatography, anion exchange chromatography, size exclusion chromatography, 2-D chromatography, enzyme-catalyzed assays, and chemical reaction assays. For purposes of the present description, "2-dimensional" or "2-D" with respect to chromatography or chromatographic analysis is intended to indicate that a sample is first passed through one chromatographic media and subsequently passed through a second, different chromatographic media. For example, 2-dimensional analysis of an amino acid may be subjected to 2-D chromatographic analysis by first passing a sample containing the amino acid through a size exclusion resin and then passing samples obtained therefrom through a cation exchange resin. Examples of 2-dimensional HPLC device include those from Agilent Technologies. See, also e.g., DX-800 Process Analyzer from Dionex Corp., Sunnyvale, Calif. In some embodiments, the analytical device is an automated enzyme-catalyzed assay or a chemical reaction, e.g., a NOVA® Bioprofiler (NOVA Biomedical, Waltham, Mass.).

At-line and on-line use of HPLC technology is also envisioned as an analytical device of the present invention. For example, integration of at-line or on-line HPLC systems may be used in performing amino acid analysis on bioreactor samples. See, e.g., Braganza, et al.

In some embodiments, the analytical device can be a kit, e.g., a test strip, which can be placed in contact with the sample to give rapid determination of the cellular concentration. In some embodiment, the kit comprises a substrate which produces a chemical and/or enzyme-linked reaction to produce a detectable signal in the presence of a surrogate marker, or a specific concentration of a surrogate marker. The detectable signal can include, e.g., a colormetric change or other visual signal. In some embodiments, the analytical device is a disposable analytical device, e.g., a disposable test strip. Such kits could be useful do to their ease of operation and their reduced costs relative to other larger, more complicated analytical devices. Such kits could also be useful during small scale cell culture propagation to determine that optimal health and productivity of the culture.

Various sample collection devices are known in the art. In some embodiments, the sample collection devices are automated, and at-line, in-line, or online. In some embodiments, the sample collection device can obtain the sample sterilely. Examples of automated sampling devices include those from, e.g., Groton Biosystems or NOVA Biomedical. Examples of bioreactors include those from Applikon.

Each of the above mentioned examples of at-line, on-line, and in-line devices provide the benefit of real-time or near real-time assessments of bioreactor culture. Such assessments may be coupled to an algorithm or algorithms in a computer controlled system wherein the data is collected and processed for use in implementing dynamic feedback control of system and process changes that will optimize or enhance bioproduct quality (including reduced product variability) and quantity.

In some embodiments, sampling and analysis of the surrogate marker can also be useful in the determination of the most efficient time to expand the cell culture, e.g., to a larger bioreactor. In some embodiments, measurement of the addition of a predetermined amount of biomarker can be used as an indicator that the cell culture should be expanded. In some embodiments, measurement of the addition of a predetermined amount of biomarker can be used as an indicator that the cell culture should be harvested.

Typical cell culture growth curves include inoculation of nutrient media with the starter cells followed by lag phase growth. The lag phase is followed by log phase growth of the culture, ultimately resulting in a plateau phase. As used herein, the term "bioreactor run" can include one or more of the lag phase, log phase, or plateau phase growth periods during a cell culture cycle. Thus, in some embodiments a method of the present invention the sampling, analyzing, processing of data, or adding additional nutrient media occurs in one or more of the lag phase, log phase, or plateau phase growth periods during a cell culture cycle. In some embodiments, the sampling, analyzing, processing of data, or adding additional nutrient media occurs in all three phases of the cell culture growth cycle.

As one of skill in the art can appreciate, different nutrients (of different concentrations of nutrients) may be required in different growth periods of a cell culture cycle. Thus, in some embodiments, a method of the present invention is directed to a method comprising (a) intermittently or continuously analyzing the concentration of one or more amino acids in the bioreactor cell culture; and (b) adding to the bioreactor cell culture additional nutrient media plus some additional growth component when the concentration of the one or more amino acids is lower than a target value, wherein the additional growth component is beneficial in a certain phase of the lifecycle.

In some embodiments, the present invention is directed to a method of efficiently producing an antibody. For example, the method can comprise: (a) sterilely extracting a sample from the bioreactor cell culture by means of an automated online sample collection device; (b) analyzing the extracted sample by means of an automated analytical device to generate data representative of the quantity of an amino acid; (c) processing the generated data by means of an algorithm or computer-based processing program wherein the processed data is used to determine an amount of additional nutrient media to add to the bioreactor; and (d) adding the amount of additional nutrient media determined in (c) to the bioreactor by means of an automated feed device.

In some embodiments of the present invention, the quantity of the bioproduct produced increases significantly relative to traditional manufacturing processes. In some embodiments, the quantity of bioproduct produced by the method of the present invention is 10% to 100% greater than the quantity of bioproduct produced by a traditional manufacturing process. In some embodiments, the quantity of bioproduct produced by the method of the present invention is 10% 15%, 20%, 25%, 30%, 35%, 40%, 45%, 50%, 55%, 60%, 65% 70%, 80%, or 90% 100% greater than the quantity of bioproduct produced by a traditional manufacturing process.

Various bioproducts are envisioned in the present invention. In some embodiments, the bioproduct is an antibody, recombinant protein, glycoprotein, or fusion protein. In some embodiments, the bioproduct is a soluble protein. In some embodiments, the bioproduct is an antibody, antibody fragment or modified antibody (e.g., a multivalent antibody, a domain-deleted antibody, a multimeric antibody, a hinge-modified antibody, a stabilized antibody, a multispecific antibody, a linear antibody, an scFv, a linked ScFv antibody, a multivalent linear antibody, a multivalent antibody without Fc, a Fab, a multivalent Fab, etc.).

The terms "bioproduct" as used herein refers to a molecule with a molecular mass exceeding 1 kDa which can be isolated from cellular culture, e.g., eukaryotic (e.g., mammalian) cell culture. In some embodiments, the term bioproduct refers to molecules with a molecular mass exceeding 50 kDa, 75 kDa, 100 kDa, 125 kDa, or 150 kDa. In some embodiments, the use of the term refers to polymers, e.g., biopolymers such as nucleic acids (such as DNA, RNA), polypeptides (such as proteins), carbohydrates, and lipids. In some embodiments, the term "bioproduct" refers to a protein. In some embodiments, the term "bioproduct" refers to a recombinant protein or a fusion protein. In some embodiments, the bioproduct is an antibody, e.g., an antibody fragment, an antigen-binding polypeptide (including, but not limited to fusion proteins), a modified antibody, a monoclonal antibody or a polyclonal antibody.

As used herein, the term "protein" is intended to encompass a singular "protein" as well as plural "proteins." Thus, as used herein, terms including, but not limited to "peptide," "polypeptide," "amino acid chain," or any other term used to refer to a chain or chains of amino acids, are included in the definition of a "protein," and the term "protein" may be used instead of, or interchangeably with, any of these terms. The term further includes proteins which have undergone post-translational modifications, for example, glycosylation, acetylation, phosphorylation, amidation, derivatization by known protecting/blocking groups, proteolytic cleavage, or modification by non-naturally occurring amino acids. Proteins also include polypeptides which form multimers, e.g., dimers, trimers, etc. The term protein also includes fusions proteins, e.g., a protein that is produced via a gene fusion process in which a protein (or fragment of a protein) is attached to an antibody (or fragment of antibody). Examples of fusion proteins of the present invention include disulfide-linked bifunctional proteins comprised of linked Fc regions from human IgG1 and human IgE; and lymphotoxin beta receptor immunoglobulin G1.

In some embodiments, the bioproduct is an antibody or antibody-like polypeptide. The term "antibody" refers to polyclonal, monoclonal, multispecific, human, humanized or chimeric antibodies, single chain antibodies, Fab fragments, F(ab')2 fragments, fragments produced by a Fab expression library, anti-idiotypic (anti-Id) antibodies (including, e.g., anti-Id antibodies to antibodies of the invention), and epitope-binding fragments of any of the above. In some embodiments, the term "antibody" refers to a monoclonal antibody. The term "antibody" also refers to immunoglobulin molecules and immunologically active portions of immunoglobulin molecules, i.e., molecules that contain an antigen binding site that immunospecifically binds an antigen. The immunoglobulin molecules that can be purified by the method of the invention can be of any type (e.g., IgG, IgE, IgM, IgD, IgA and IgY), class (e.g., IgG1, IgG2, IgG3, and IgG4) or subclass of immunoglobulin molecule. Antibodies of the present invention also include chimeric, single chain, and humanized antibodies. Examples of antibodies of the present invention include commercialized antibodies, such as natalizumab (humanized anti-a4 integrin monoclonal antibody), humanized Anti-Alpha V Beta 6 monoclonal antibody, humanized anti-VLA1 IgG1 kappa monoclonal antibody; and huB3F6 (humanized IgG1/kappa monoclonal antibody).

Antibodies produced by the method of the invention originate from any animal origin including birds and mammals. In some embodiments, the antibodies purified by the method of the invention are human, murine (e.g., mouse and rat), donkey, ship rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins. See, e.g., U.S. Pat. No. 5,939,598 by Kucherlapati et al. In some embodiments, the term "antibody" includes, but is not limited to, IgG1, IgG2, IgG3, and IgG4 antibodies, including commercialized antibodies.

Antibodies produced by the method of the invention include, e.g., native antibodies, intact monoclonal antibodies, polyclonal antibodies, multispecific antibodies (e.g., bispecific antibodies) formed from at least two intact antibodies, antibody fragments (e.g., antibody fragments that bind to and/or recognize one or more antigens), humanized antibodies, human antibodies (Jakobovits et al., Proc. Natl. Acad. Sci. USA 90:2551 (1993); Jakobovits et al., Nature 362:255-258 (1993); Bruggermann et al., Year in Immunol. 7:33 (1993); U.S. Pat. Nos. 5,591,669 and 5,545,807), antibodies and antibody fragments isolated from antibody phage libraries (McCafferty et al., Nature 348:552-554 (1990); Clackson et al., Nature 352:624-628 (1991); Marks et al., J. Mol. Biol. 222: 581-597 (1991); Marks et al., Bio/Technology 10:779-783 (1992); Waterhouse et al., Nucl. Acids Res. 21:2265-2266 (1993)). The antibodies produced by the method of the invention may be recombinantly fused to a heterologous polypeptide at the N- or C-terminus or chemically conjugated (including covalently and non-covalently conjugations) to polypeptides or other compositions. For example, antibodies produced by the method of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

In some embodiments, the bioproduct of the present invention is pharmaceutically acceptable. "Pharmaceutically acceptable" refers to a bioproduct that is, within the scope of sound medical judgment, suitable for contact with the tissues of human beings and animals without excessive toxicity or other complications commensurate with a reasonable benefit/risk ratio.

Methods of the invention can also be used, for example, to render accurate predictions of appropriate timing/amount for transfer of nutrient media for a second bioreactor cell culture based on the timing/amount for transfer of nutrient media in a first cell culture. For example, calculations in the first bioreactor can be used in the next bioreactor in a culture train (instead of relying on off-line cell count measurements and subsequent calculations therefrom). Thus, in some embodiments, the present invention can be directed to a method of increasing production in subsequent bioreactor cell culture. For example, some embodiments of the invention can be directed to a method of enhancing the quantity of therapeutic protein or antibody produced, or decreasing therapeutic protein or antibody production time, in a bioreactor cell culture producing the therapeutic protein or antibody, the method comprising: (a) producing a first bioreactor cell culture by: (i) extracting a sample from the bioreactor by means of an automated online sample collection device; (ii) analyzing the extracted sample by means of an automated analytical device to generate data representative of the quantity of a nutrient, or other surrogate marker; (iii) processing the generated data by means of an algorithm or computer-based processing program wherein the processed data is used to determine an amount of additional nutrient media to add to the bioreactor; (iv) adding the amount of nutrient media determined in (iii) to the bioreactor by means of an automated device; and (v) recording the time and amount of each nutrient media addition; and (b) producing a second bioreactor cell culture, wherein the time and amount of each nutrient media addition in the second bioreactor cell culture is determined from the time and amount of each nutrient media addition in the first bioreactor cell culture. In some embodiments, the bioreactor of the first cell culture is smaller than the bioreactor of the second cell culture. Thus, e.g., a small bioreactor cell culture can be used in development of the cell culture conditions using the method of the present invention, then that feeding strategy can be applied to a manufacturing-scale bioreactor for large-scale production.

Methods of the present invention afford the advantage of providing enhanced insight into critical process parameters; such as in bioreactor cell culture process, where such systems and methods may afford the ability to identify and manage some, or perhaps all, sources of variability and to accurately and reliably predict and affect in-process product quality attributes. Additional benefits of the present invention also include: 1) enhanced understanding of cell cultivation and protein production bioprocesses; 2) identification and correction of nutritional parameters indicative of bioprocess variability; and 3) reduction of bioprocess testing burdens.

The invention can also be directed to a bioproduct produced by the methods of the present invention.

EXAMPLES

Example 1

Determination of Amino Acid Profiles in Traditional Manufacturing Process

Figure 1:
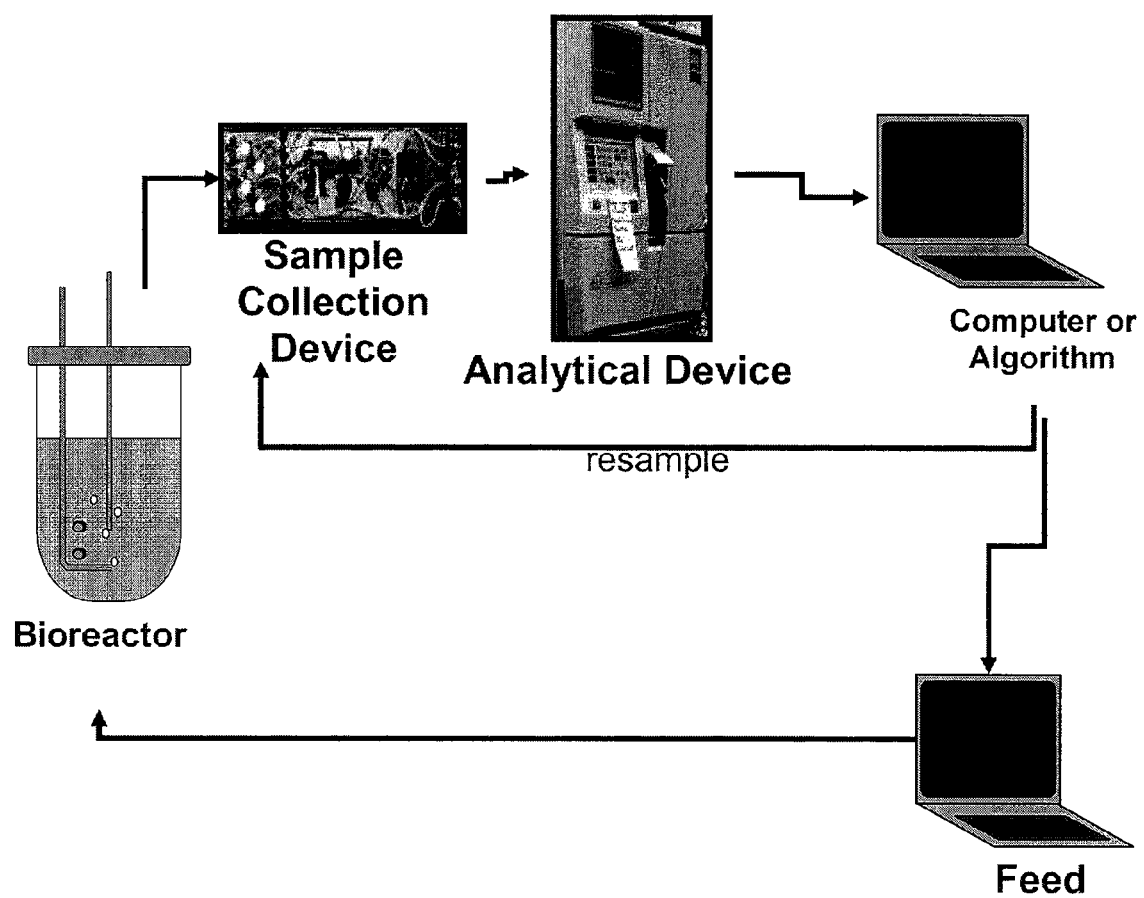
FIG. 1 represents a schematic flow chart of a method of the present invention.
Figure 2:
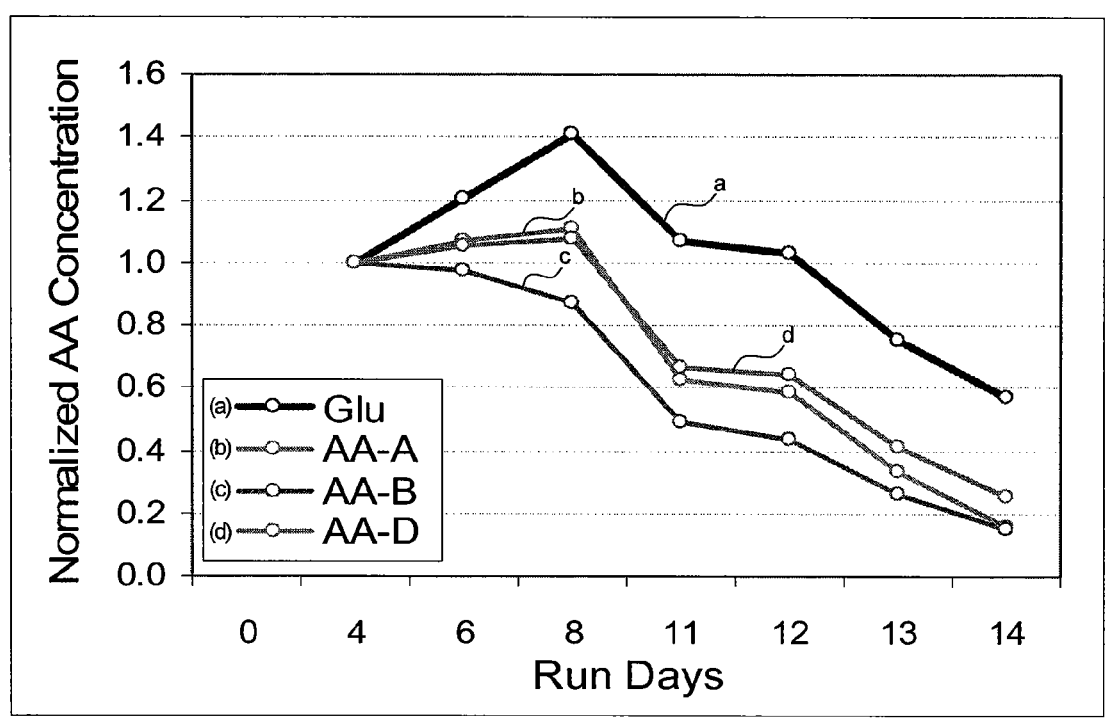
FIG. 2 represents the amino acid concentrations during a bioreactor run using a traditional manufacturing process.

Traditional manufacturing processes incorporate adding a bolus feed of a single nutrient, or a nutrient media at predetermined times. CHO cells expressing a monoclonal antibody were produced using a traditional manufacturing process. During the bioreactor run, samples were taken and the concentration of glucose and three different amino acids was determined. See FIG. 2. The data indicates that during a bioreactor run using a traditional manufacturing process, the normalized amino acid concentration decreases significantly, by 60%-80% after 14 days. Likewise, the glucose concentration varies throughout the bioreactor run. Thus, the traditional manufacturing feeding process was not sufficient to maintain stabilized nutrient levels.

Example 2

Determination of Online Feedback Glucose Control and Glutamate Control

Figure 3A:
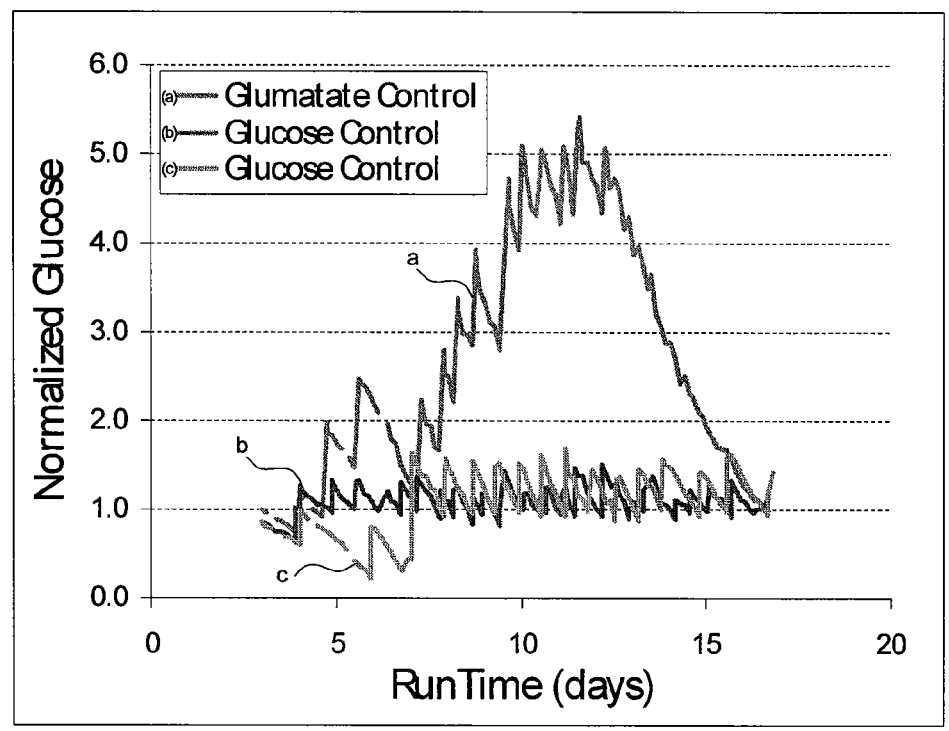
FIG. 3A represents the glutamate and glucose concentrations in a bioreactor run, wherein the glucose is maintained above a target level by addition of nutrient media.
Figure 3B:
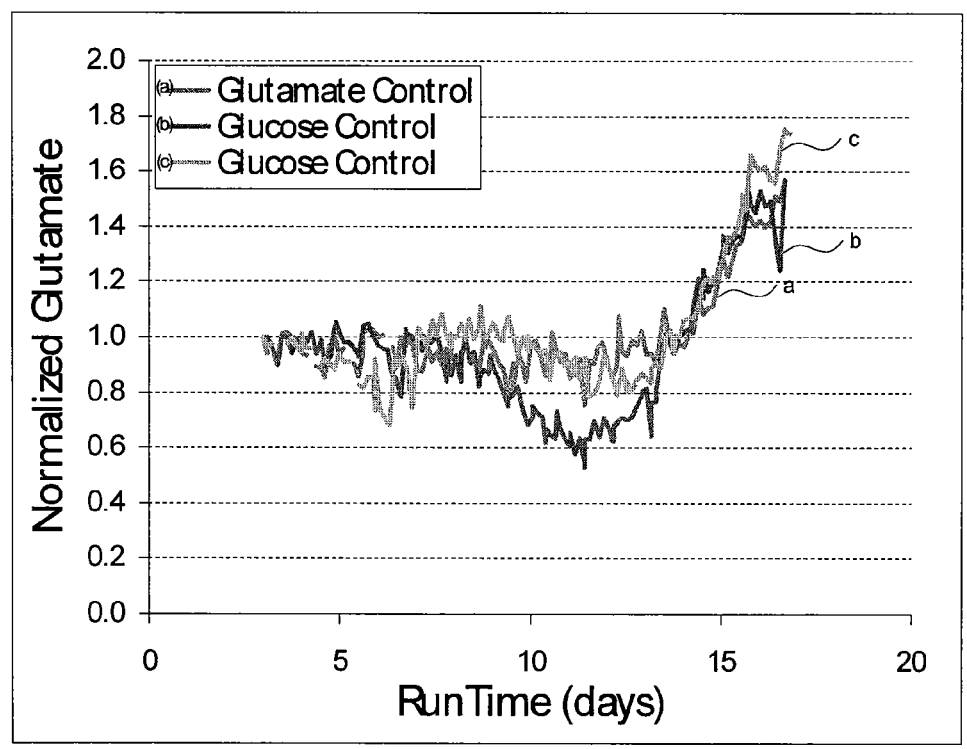
FIG. 3B represents the glutamate and glucose concentrations in a bioreactor run, wherein the glutamate is maintained above a target level by addition of nutrient media.

CHO cells expressing a monoclonal antibody were produced using an on-line feedback control process to determine the feeding strategy. During the bioreactor run, samples of the cell culture were taken every 3 hours using a NOVA online autosample (NOVA Biomedical). The samples were immediately analyzed to determine glucose concentrations and glutamate concentrations using a NOVA Bioprofiler device (NOVA Biomedical). Two different bioreactor runs were performed. In the first bioreactor run, total nutrient media was added throughout the bioreactor run such that glucose concentration levels were maintained above the original glucose levels (glucose control process). See, FIG. 3A. In the second bioreactor run, total nutrient media was added throughout the bioreactor run such that glutamate concentration levels were maintained above the original glutamate levels (glutamate control process). See, FIG. 3B. In the glucose control process, the concentration of glutamate varied widely throughout the bioreactor run, at times being as much as 5× higher than the starting concentration of glutamate. In the glutamate control process, the values of both the glutamate and the glucose remain more stable.

Example 3

Figure 4A:
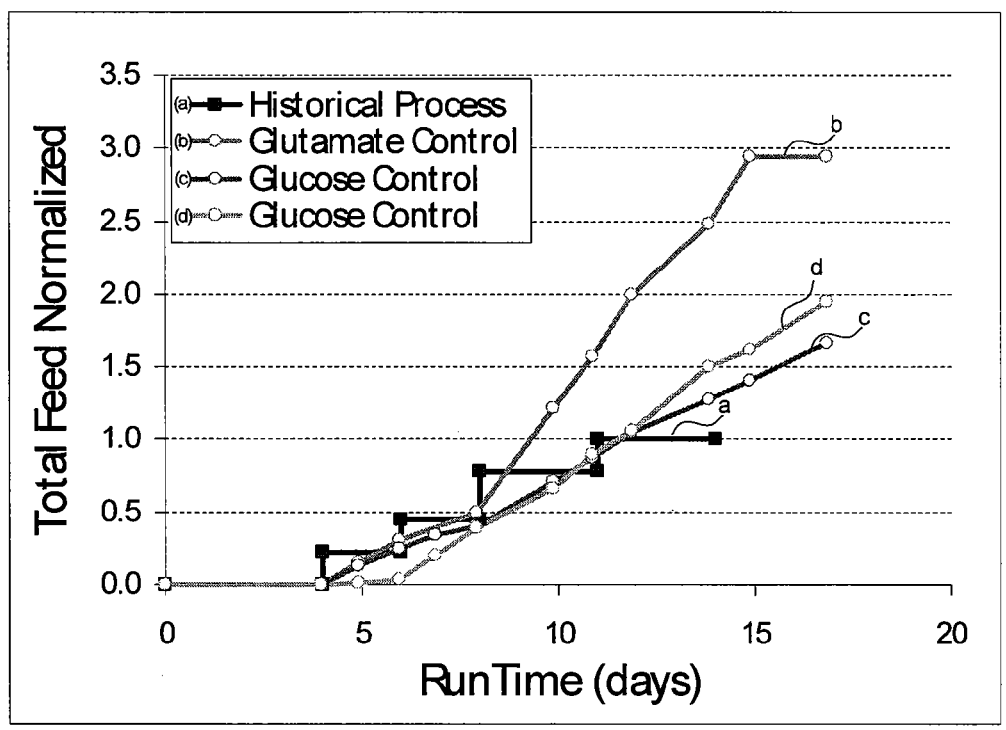
FIG. 4A represents the total nutrient media required for a biological run under: (a) a traditional manufacturing process, (b) a glucose controlled process, and (c) a glutamate controlled process.

Nutrient Media and Antibody Production Using Glucose Control and Glutamate Control The total quantity of nutrient feed was determined for a traditional manufacturing process, a glucose control process, and a glutamate control process. See FIG. 4A. The traditional manufacturing process consumed the least amount of total nutrient media. The glucose control process consumed 1.8× more total nutrient media relative to the traditional manufacturing process. The glutamate process consumed 3× more total nutrient media.

Figure 4B:
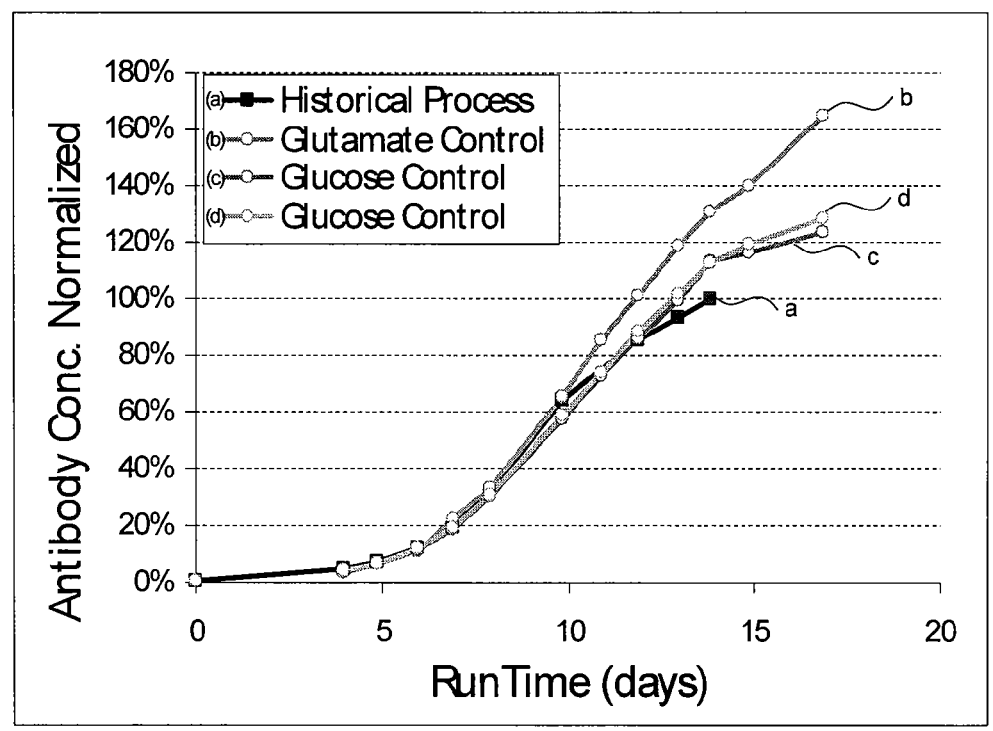
FIG. 4B represents antibody production under: (a) a traditional manufacturing process, (b) a glucose controlled process, and (c) a glutamate controlled process.

Monoclonal antibody production was tested using a traditional manufacturing process, a glucose control process, and a glutamate control process. See FIG. 4B. The antibody titer of the glucose control process increased 15% within the same culture duration, and 25% overall relative to the traditional manufacturing process. The antibody titer of the glutamate control process increased 35% within the same culture duration, and 60% overall relative to the traditional manufacturing process.

Example 4

Translation of Automatic Feedback Strategy to a Manufacturing Process

The feeding strategy (volume of nutrient media and timing of feeds) of a first bioreactor run utilizing the glutamate controlled sampling/feedback method of the present invention was translated into daily pre-defined manual bolus total nutrient media additions in a subsequent second bioreactor run. The feeding strategies of the first and second bioreactors runs were compared to a traditional manufacturing process. The total glucose amounts for the first bioreactor run, the second bioreactor run, and the traditional manufacturing process are provided in FIG. 5A. Similar titers were achieved in the second bioreactor run using the manual pre-defined feed strategy based on the sampling/feedback method of the first bioreactor run. See, FIG. 5B. The data indicates that the sample/feedback method can be used to develop feeding strategies for future bioreactor runs, even if the sample/feedback methods are not utilized in the future runs. This could be particularly useful in manufacturing, where on-line feedback control is not currently available.

Example 5

Application of Feed Strategy to Second Bioreactor Cell Culture

The glutamate control feeding strategy of a first bioreactor run utilizing the sampling/feedback method of the present invention was applied into an automatic feeding method in a subsequent second bioreactor run. Both the first and second bioreactor runs utilized the same CHO cell host and the same nutrient media. The total glucose amounts for the first bioreactor run and the second bioreactor run are provided in FIG. 5A. Using the automatic feeding device in the second bioreactor run, the feeding strategy in from the first bioreactor run, similar titers were achieved.

FIG. 5A compares (a) the total feed added in a traditional manufacturing process, (b) the total feed added in a automatic sampling/feedback control process of the present invention, and (c) a manual feed process utilizing the feeding strategy developed from an automatic sampling/feedback control process. FIG. 5B compares (a) the antibody concentration in the bioreactor produced in a traditional manufacturing process, (b) the antibody concentration in the bioreactor produced in a automatic sampling/feedback control process of the present invention, and (c) a manual feed process utilizing the feeding strategy developed from an automatic sampling/feedback control process. Methods (b) and (c) produced significantly greater quantities of antibody compared to the traditional manufacturing process.

Example 6

Nutrient Media and Antibody Production Using Valine and Lysine Controls

CHO cells expressing a monoclonal antibody were cultured in a bioreactor run. Manual HPLC measurements were performed once-a-day to determine valine concentrations. Based on these measurements, nutrient feed was added in an amount predicted to maintain a concentration of at least 3 mM valine through day 10. From day 11 onward, nutrient feed was added at a level predicted to maintain at least 2 mM valine. A second experiment was run in parallel in which lysine was measured daily using HPLC, and nutrient feed was added in order to maintain a concentration of at least 3 mM lysine (up to day 10) or of at least 2 mM lysine (day 11 and onward). In addition, a control traditional manufacturing process ("Cycle 1 Average") was performed in parallel.

The viable cell density and glucose concentrations over time were measured, and the results are shown in FIGS. 7A and 7B. The results of the lysine and valine control processes were similar to results obtained using the glutamate control processes described above in that both the lysine and valine control processes used more nutrient feed than the traditional manufacturing process control. FIGS. 7C and 8A. The lysine control process consumed more feed than any of the other conditions. In addition, the antibody titer produced from each of the valine and lysine control processes was higher than that antibody titer produced from the traditional manufacturing process. FIG. 7C. Similarly, the specific productivity rate (SPR), measured in picograms of antibody secreted per cell per day, was also higher in each of the valine and lysine control processes than in the traditional manufacturing process. FIG. 7C. In addition, the cumulative integrated cell growth (cICG) was also measured, and the results are shown in FIG. 7C. The concentration of glutamate was also measured throughout each of the experiments. FIG. 8B.

In some experiments, it was noted the valine and lysine consumption rates increased as more feed was added. Therefore, in these experiments, despite efforts to maintain the concentration of these amino acids above a target threshold (2 or 3 mM), the measured concentrations dropped below the target values. In order to maintain valine or lysine levels at the appropriate target level, concentrations could be measured more frequently (i.e. more than once a day) and nutrient feed added accordingly. Alternatively, a pre-defined feed strategy based, similar to that described in Example 4, could be used.

In these experiments, a second antibody-producing CHO cell culture is initiated, and the valine and lysine concentrations measured in a first experiment are used to determine the appropriate amount of nutrient feed to add to the second culture in order to maintain at least 2-3 mM valine or lysine. The valine and lysine concentrations in the second culture are measured over time to show that they are maintained above the target threshold level, and an increase in antibody titer demonstrates that valine and lysine can be used as monitors for feedback control.

Example 7

Decoupling Feed Volume From Surrogate Marker Triggers

The automated glutamate feedback control process gave significantly improved results as compared to the traditional manufacturing process. However, in each of the feedback control processes, a higher feed volume was required. Therefore, the following experiment was performed in order to determine if the increased performance was due to the increase in feed volume or due to the addition of nutrient feed at specific times determined by feedback control.

In these experiments, total feed volume from the glutamate controlled condition was used, and it was converted into extra feed volume in two ways. In the first method (bolus extra feed), the amount of nutrient feed added was determined based on the proportion of the feed taken from the cycle-1 (traditional) process. For example, if the total feed volume from the glutamate control process was 2000 mL, and the cycle-1 (traditional) process designates the first feed volume to be 10% of the total feed volume, then 200 mL was given for the first feed. In the second method (daily extra feed), the amount of nutrient feed added was determined based on the total feed volume divided into equal volumes over the course of the run. Feeds were added from day 4 to day 16. The results of these experiments are shown in FIG. 9. The results demonstrate that even though similar total feed volumes were used in each of the conditions, the automated glutamate control process produced a much higher antibody titer than either the bolus extra feed or the daily extra feed processes. FIG. 9F. Therefore, the improved results of the feedback control process is not simply do to increased total feed volume. Instead, the improved results are due to the adding nutrient feed at times and amounts based on feedback control.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. An automated method of increasing the quantity of a bioproduct produced, or decreasing bioproduct production time, in a bioreactor cell culture process, the method comprising:

(a) intermittently or continuously analyzing one or more carbohydrates or vitamins in the bioreactor cell culture by means of an automated sampling device to generate data representative of the concentration of said one or more carbohydrates or vitamins;
(b) processing said data by means of a computer-based processing program to determine an amount of nutrient media to add to the bioreactor; and,
(c) adding said amount of nutrient media determined in (b) to the bioreactor cell culture by means of an automated feed device when the concentration of said one or more carbohydrates or vitamins is below a target value.

2. The method of claim 1, wherein nutrient media is added to the bioreactor cell culture based on analysis of the concentration of only one type of carbohydrate or vitamin.

3. The method of claim 2, wherein the carbohydrate or vitamin is partially or wholly consumed during the bioreactor cell culture process.

4. The method of claim 1, wherein said one or more carbohydrate is selected from the group consisting of: glucose, galactose, maltose, fructose, and combinations thereof.

5. The method of claim 1, wherein said one or more vitamin is selected from the group consisting of: a B group vitamins, vitamin A, vitamin E, riboflavin, thiamine, biotin, and combinations thereof.

6. The method of claim 1, wherein the cells in the bioreactor cell culture comprise Chinese Hamster Ovary (CHO) cells.

7. The method of claim 1, wherein the bioproduct comprises an antibody, antibody fragment, or antigen-binding polypeptide.

8. The method of claim 1, wherein said nutrient media is added to the bioreactor cell culture in an amount sufficient to maintain a substantially stable concentration of said one or more carbohydrates or vitamins throughout the bioreactor cell culture process.

9. The method of claim 1, where steps (a) to (c) are repeated greater than 10 times throughout the bioreactor cell culture process.

10. The method of claim 1, wherein steps (a) to (c) are repeated a number of times in a range selected from the group consisting of:
(a) about every 4 minutes to about every 18 hours throughout the bioreactor cell culture process;
(b) about every 10 minutes to about every 6 hours throughout the bioreactor cell culture process;
(c) about every 1 minute to about every hour throughout the bioreactor cell culture process;
(d) about every 1 minute to about every 30 minutes throughout the bioreactor cell culture process;
(e) about every 1 minute to about every 15 minutes throughout the bioreactor cell culture process; and
(f) about every 1 minute to about every 10 minutes throughout the bioreactor cell culture process.

11. The method of claim 1, wherein the bioreactor cell culture process utilizes media selected from group consisting of:
a) serum-free media;
b) protein-free media; and
c) chemically defined media.

12. The method of claim 1, wherein said one or more carbohydrates or vitamins is analyzed by one or more means selected from the group consisting of:
(a) off line sample analysis;
(b) on-line sample analysis;
(c) in-line sample analysis; and
(d) at-line sample analysis.

13. The method of claim 12, wherein the automated sampling device is one or more apparatuses used to monitor an assay selected from the group consisting of:
(a) enzyme-catalyzed assays; and
(b) chemical reaction assays.

14. The method of claim 12, wherein the automated sampling device is one or more apparatuses used to perform one or more types of chromatographic analysis selected from the group consisting of:
 a) gas chromatography;
 b) liquid chromatography;
 c) affinity chromatography;
 d) supercritical fluid chromatography;
 e) ion exchange chromatography;
 f) size-exclusion chromatography;
 g) reversed phase chromatography;
 h) two-dimensional chromatography;
 i) fast protein (FPLC) chromatography;
 j) countercurrent chromatography;
 k) chiral chromatography; and
 l) aqueous normal phase (ANP) chromatography.

15. An automated method of enhancing the quantity of a bioproduct produced, or decreasing bioproduct production time, in a bioreactor cell culture producing the bioproduct, the method comprising:
(a) performing a first bioreactor cell culture process by:
 (i) analyzing a bioreactor sample by means of an automated analytical device to generate data representative of the quantity of one or more carbohydrates or vitamins;
 (ii) processing said data by means of computer-based processing program to determine an amount of nutrient media to add to the bioreactor;
 (iii) adding said amount of nutrient media determined in (ii) to the bioreactor cell culture by means of an automated feed device when the quantity of said one or more carbohydrates or vitamins is below a target value; and
 (iv) recording the time and amount of each nutrient media addition; and
(b) performing a subsequent bioreactor cell culture process, wherein the time and amount of each nutrient media addition in the subsequent bioreactor cell culture process is determined based on the time and amount of each nutrient media addition in the first bioreactor cell culture process.

16. The method of claim 15, wherein the bioreactor of the first cell culture is smaller than the bioreactor of the subsequent cell culture.

* * * * *